US009422368B2

(12) United States Patent
Spee et al.

(10) Patent No.: US 9,422,368 B2
(45) Date of Patent: Aug. 23, 2016

(54) HUMANIZED ANTI-HUMAN NKG2A MONOCLONAL ANTIBODY

(71) Applicant: NOVO NORDISK A/S, Bagsvaerd (DK)

(72) Inventors: Petrus Johannes Louis Spee, Allerod (DK); Jianhe Chen, Beijing (CN); Soren Berg Padkjaer, Vaerlose (DK); Jing Su, Beijing (CN); Jinchao Zhang, Beijing (CN); Jiujiu Yu, Zhejiang (CN)

(73) Assignee: NOVO NORDISK A/S, Bagsvaerd (DK)

( * ) Notice: Subject to any disclaimer, the term of this patent is extended or adjusted under 35 U.S.C. 154(b) by 0 days.

(21) Appl. No.: 14/449,346

(22) Filed: Aug. 1, 2014

(65) Prior Publication Data

US 2014/0341896 A1  Nov. 20, 2014

Related U.S. Application Data

(62) Division of application No. 12/811,990, filed as application No. PCT/EP2009/050795 on Jan. 23, 2009, now Pat. No. 8,796,427.

(60) Provisional application No. 61/025,923, filed on Feb. 4, 2008.

(30) Foreign Application Priority Data

Jan. 24, 2008 (EP) .................................... 08150601

(51) Int. Cl.
*A61K 39/395* (2006.01)
*C07K 16/28* (2006.01)

(52) U.S. Cl.
CPC ......... *C07K 16/2851* (2013.01); *C07K 16/2803* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,489,525 | A | 2/1996 | Pastan |
| 5,876,950 | A | 3/1999 | Siadak et al. |
| 5,994,524 | A | 11/1999 | Matsushima et al. |
| 8,206,709 | B2 | 6/2012 | Spee et al. |
| 2003/0095965 | A1 | 5/2003 | Van Beneden et al. |
| 2003/0171280 | A1 | 9/2003 | Soderstrom |
| 2005/0037002 | A1 | 2/2005 | Velardi et al. |
| 2009/0208416 | A1 | 8/2009 | Moretta et al. |
| 2011/0052606 | A1 | 3/2011 | Spee et al. |
| 2011/0229486 | A1 | 9/2011 | Moretta et al. |

FOREIGN PATENT DOCUMENTS

| | | |
|---|---|---|
| CN | 1747969 A | 3/2006 |
| CN | 101107269 A | 1/2008 |
| EP | 1036327 A2 | 9/2000 |
| JP | 03112485 A | 5/1991 |
| JP | 03112486 A | 5/1991 |
| JP | 03112487 A | 5/1991 |
| JP | 2004-528824 A | 9/2004 |
| JP | 03112484 U | 8/2005 |
| WO | 99/28748 A2 | 6/1999 |
| WO | 01/71005 A2 | 9/2001 |
| WO | WO 02/05122 | 1/2002 |
| WO | 02/50122 | 6/2002 |
| WO | 03/008449 A1 | 1/2003 |
| WO | 03/095965 A2 | 11/2003 |
| WO | 2004/003019 A2 | 1/2004 |
| WO | 2004/056312 | 7/2004 |
| WO | 2005/009465 A1 | 2/2005 |
| WO | 2005/105849 A1 | 11/2005 |
| WO | 2006/070286 | 7/2006 |
| WO | 2007042573 A2 | 4/2007 |
| WO | 2008/009545 | 1/2008 |
| WO | 2009/092805 A1 | 7/2009 |

OTHER PUBLICATIONS

Marin et al., Immunogenetics. Feb. 2003;54(11):767-75.*
Palmisan et al., Hum Immunol. Jan. 2005;66(1):1-12.*
Sandberg et al., Proc Natl Acad Sci U S A. Feb. 8, 2005;102(6):2052-7.*
Majumbder et al. (Leuk Res. Feb. 2006;30(2):242-5).*
Arina et al., Expert Opinion on Biological Therapy, 7:5, 599-615 (2007).*
Melero et al. (Nat Rev Cancer. Feb. 2007;7(2):95-106).*
Lee et al., Proc. Natl. Acad. Sci. USA, vol. 95, pp. 5199-5204, Apr. 1998.*
Li et al., Proc. Natl. Acad. Sci. USA vol. 95, pp. 4894-4899, Apr. 1998.*
Borrego et al., "The CD94/NKG2 Familty of Receptors," Imm. Res., 2006, vol. 35, No. 3, pp. 263-277.
Lee et al., "HLA-E is a Major Ligand for the Natural Killer Inhibitory Receptor CD94/NKG2A," PNAS USA, 1998, vol. 95, pp. 5199-5204.
Aldrich et al., "Identification of Tap-Dependent Leader Peptide Recognized by Alloreactive T Cells Specific for a Class Ib Antigen," Cell, 1994, vol. 79, pp. 649-658.
Aramburu et al., "A Novel Function Cell Surface Dimer (Kp43) Expressed by Natural Killer Cells and T Cell Receptor-Gamma/Delta+ T Lymphocytes," The Journal of immunology, 1990, vol. 144, No. 8, pp. 3238-3247.

(Continued)

*Primary Examiner* — Zachary Skelding
(74) *Attorney, Agent, or Firm* — Saliwanchik, Lloyd & Eisenschenk

(57) ABSTRACT

The present invention relates to agents that are non-competitive antagonists of the CD94/NKG2A receptor such as certain anti-NKG2A antibodies, in particular humanized versions of murine anti-NKG2A antibody Z199, as well as methods of producing and using such agents and antibodies.

1 Claim, 8 Drawing Sheets

(56) References Cited

OTHER PUBLICATIONS

Borrego, Francisco et al., "Recognition of Human Histocompatability Leukocyte Antigen (HLA)-E Complexed with HLA Class I Signal Sequence-Derived Peptides by CD94/NKG2 Confers Protection from Natural Killer Cell-Mediated Lysis", Journal of Experimental Medicine, Mar. 2, 1998, vol. 187, No. 5, pp. 813-881.
Braud et al, TAP-and tapasin-dependent HLA-E Surface Expression Correlates with the Binding of an MHC Class Leader Peptide, Current Biology, 1998, vol. 8, No. 1, pp. 1-10.
Braud et al., "The Human Major Histocompatibility Complex Class Ib Molecule HLA-E Binds signal Sequence-derived Peptides with Primary Anchor Residues at Position 2 and 9," Eur. J. Immunol., 1997, vol. 27, pp. 1164-1169.
Braud et al., "HLA-E Binds to Natural Killer Cell Receptors CD94/ NK02A, B and C," Nature (London), 1998, vol. 391, Vo. 6669, pp. 795-799.
Brooks et al., "Specific Recognition of HLA-E, But Not Classical, HLA Class I Molecules by Soluble CD94/NKG2A and NK Cells," Jouranl of Immunology, 1999, vol. 162, pp. 305-315.
Houchins et al., "DNA Sequence Analysis of NKG2, a Family of Related cDNA Clones Enclosing Type II Integral Membrane Proteins on Human Natural Killer Cells", J. Exp. Med., 1991, vol. 173, pp. 1017-1020.
Houchins et al., Natural Killer Cell Cytolytic Activity is Inhibited by NKG2-A and Activated by NKG2-C, The Journal of Immunology, 1997, vol. 158, pp. 3603-3609.
Lanier et al., "Arousal and Inhibition of Human NK Cells," Immunological Reviews, 1997, vol. 155, pp. 145-154.
Lanier et al., Immunoreceptor DAP12 Bearing a Tyrosine-Based Activation Motif is Involved in Activiating NK Cells, Nature 1998, vol. 391, pp. 703-707.
Lazetic et al., "Human Natural Killer Cell Receptors Involved in MHC Class I Recognition are Disulfide-Linked Heterokimers of CD94 and NKG2 Subunits," The Journal of Immunology, 1996, vol. 157, pp. 4741-4745.
Lee et al., "HLA-E Surface Expression Depends on Binding of TAP-Dependent Peptides Derived from Certain HLA Class I Signal Sequences," The Journal of Immunology, 1998, vol. 160, pp. 4951-4960.
Leibson, Paul J., "Cytotoxic Lymphocyle Recognition of HLA-E: Utilizing a Nonclassical Window to Peer into Classical MHC," Immunity, 1998, vol. 9, No. 3, pp. 289-294.
Llano et al., "HLA-EBound Peptides Influence Recognition by Inhibitory and Triggering CD94/NKG2 Receptors, Preferential Response to an HLQ-G Derived Nonamer," European Journal Immunology, 1998, vol. 29, No. 9, pp. 2854-2863.
O'Callaghan et al., "Structure and Funtion of the Human MHC Class lb Molecules HLA-E, HLA-F and HLA-G," Immunol. Rev., 1998, vol. 163, pp. 129-138.
O'Callaghan et al., Structural Features Impose Tight Peptides Binding Specifically in teh Nonclassical MHC Molecule HLA-E, Molecular Cell, 1998, vol. 1, No. 4, pp. 531-541.
Perez-Villar et al., "Functional Ambivalence of the Kp43 (CD 94) NK Cell-Associated Surface Antigen," The Journal of Immunology, 1995, vol. 154, pp. 5779-5788.
Phillips et al., "CD94 and a Novel Associated Protein (94AP) Form a NK Cell Receptor Involved in the Recognition of HLA-A, HLA-B and HLA-C Allotypes," Immunity, 1996, vol. 5, pp. 163-172.
Plougastel et al., "Cloning of NKG2-F, a New Member of the NKG2 Family of Human Natural Killer Cell Receptor Genes," Eur. J. Immunol., 1997, vol. 27, pp. 2835-2839.
Posch et al., "HLA-E is the Ligand for the Natural Killer Cell CD94/ NK02 Receptors," Journal of Biomedical Science, 1998, vol. 5, No. 5, pp. 321-331.
Shawar et al., "Antigen Presentation by Major Histocompatibility Complex Class I-B Molecules," Annual Review of Immunology, 1994, vol. 12, pp. 839-880.
Sivori et al., "Inhibitory CD94 Molecules Identified by the Z199 Monoclonal Antibody Recognize Different HLA-Class I Molecules," Transplantation Proceedings, 1996, vol. 28, No. 6, pp. 3199-3203.

Ulbrecht et al., "The HLA-E Gene Encodes Two Differently Regulated Transcripts and a Cell Surface Protein," The Journal of Immunoloty, 1992, vol. 149, No. 9, pp. 2945-2953.
Ulbrecht et al., "Impaired Intracellular Transport and Cell Surface Expression of Nonpolymorphic HLA-E Evidence for Inefficient Peptide Building," J Exp Med, 1992, vol. 176, pp. 1083-1090.
Marshak-Rothstein et al., "Hybridoma proteins expressing the predominant idiotype of the antiazophenylarsonate response of A/J mice," PNAS, 1980, vol. 77, pp. 1120-1124.
Arturo Casadevall et al., "Immunoglobulin Isotype Influences Affinity and Specificity," Proc Natl Acad Sci USA, 2012, vol. 109, No. 31, pp. 12272-12273.
Biochemistry, "http://biochemistry.ru/biohimija_severina/ B5873content.html", 2003.
Roit et al., New methods of Immunoassay, 1991, pp. 65-75.
Roitt et al, Immunology, 2000, pp. 106-111.
Roitt et al, Immunology, 2000, pp. 530-535.
Singer et al., Genes and Genomes, 1998, vol. 1, pp. 63.
NCBI Database, "Gene Bank IDS GI:20981680", dated Apr. 3, 2013.
NCBI Database, "Gene Bank IDS GI:116013", dated May 29, 2013.
Paul, Fundamental Immunology, 3rd Edition, 1993, pp. 292-295.
Brown et al, J. Immunol. 1996; 156(9):3285-91.
Demotte et al. Eur. J. Immunol. vol. 32: p. 1688-1697, 2002.
Vitale et al, 2004, J. Exp. Med. vol. 34: p. 455-460.
Bottino et al. 2001. J. Exp. Med. vol. 194: p. 235-246.
PNAS information for Authors, 2013, p. i-iv.
Mavillio et al. Nov. 2003, PNAS vol. 100: p. 15011-15016.
Soderstrom et al. CD94/NKG2 is the Predominant Inhibitory. J of Immunology. 1997 vol. 159 pp. 1072-1075, Abstract.
Bouteiller le et al., Research in Immunology, "Antigen-Presenting Function(s) of the Non-Classical HLA-E,-F and -G Class I Molecules: The Beginning of a Story", 1996, vol. 147, No. 5, pp. 301-313.
Roque et al. Biotechnology Progress. "Antibodies and Genetically Engineered Related Molecules" 2004 vol. 20(3) pp. 639-654.
Mingari, M.C et al., International Immunology, "Cytolytic I Lymphocytes Displaying Naturla Killer . . . ", 1995, vol. 7, No. 4, pp. 697-703.
Yawata M et al., Critical Reviews in Immunology, "Variation Within the Human Killer Cell Immunoglobulin-Like Receptor(KIR) Gene Family", 2002, vol. 22, No. 5&6, pp. 463-482.
Van Beneden et al., Journal of Immunology, "Expression of LY49E and CD94/NKG2 on Fetal and Adult NK Cells", 2001, vol. 166, Number , pp. 4302-4311.
Zambello R et al., Blood, "Expression and Function of KIR and Natural Cytotoxicity Receptors in NK-Type Lymphoproliferative Diseases of Granular Lymphocytes", 2003, vol. 102, Number , pp. 1797-1805.
Downs, S et al. "Development of Antibodies Specific for NKG2 Family Members." 2011. Depts. of Monoclonal Antibodies and antibody applications,R&D Systems Inc,Minneapolis MN,USA.
Sharma et al., The Journal of Pharmacology and Experimental Therapeutics, "Comparative Pharmacodynamics of Keliximab and Clenoliximab in Transgenic Mice Bearing Human CD4", 2000, vol. 293, No. 1, pp. 33-41.
Ravetch et al., Science, "Immune Inhibitory Receptors", 2000, vol. 290, Number -, pp. 84-89.
Ralph Mocikat et al., Immunity, "Natural Killer Cells Activated by MHC Class ILOW Targets Prime Dendritic Cells to Induce Protective CD8 T Cell Responses", 2003, vol. 19, No. 4, pp. 561-569.
O'Neill et al., Blood, "Manipulating Dendritic Cell Biology for the Active Immunotherapy of Cancer", 2004, vol. 104, No. 8, pp. 2235-2246.
Bouteiller PL et al., Proceedings of the National Academy of Sciences of the USA , "Engagement of CD160 Receptor by HLA-C is a Triggering Mechanism Used by Circulating Natural Killer (NK) Cells to Mediate Cytotoxicity", 2002, vol. 99, No. 26, pp. 16963-16968.
Brooks et al., Journal of Experimental Medicine, "NKG2A Complexed With CD94 Defines a Novel Inhibitory Natural Killer Cell Receptor", 1997, vol. 185, No. 4, pp. 795-800.
Carretero M et al., European Journal of Immunology, "Specific Engagement of the CD94/NKG2-A Killer Inhibitory Receptor by the

(56) References Cited

OTHER PUBLICATIONS

HLA-E Class IB Molecule Induces SHP-1 Phosphatase Recruitment to Tyrosine-Phosphorylated NKG2-A: Evidence . . . ", 1998, vol. 28, No. 4, pp. 1280-1291.
Casadevall A et al., Nature Reviews Microbiology, "Passive Antibody Therapy for Infectious Diseases", 2004, vol. 2, No. 9, pp. 695-703.
Coiffier B et al, The Hematology Journal, "Dose Intensity or Monoclonal Antibody I First-Line Treatment", 2004, vol. 5, Number -, pp. S154-S158.
Fang M et al., Immunity, "CD94 Is Essential for NK Cell-Mediated Resistance to a Lethal Viral Disease", 2011, vol. 34, Number , pp. 579-589.
Gatto et al., Current medical Chemistry-Anti cancer Agents, "Mono Clonal Antibodies Cancer Theraphy", 2004, vol. 4, No. 5, pp. 411-414.
Hinoda et al., Cancer Science, "Monoclonal Antibodies as Effective Therapeutic Agents for Solid Tumors", 2004, vol. 95, No. 8, pp. 621-625.
Kaiser B K et al., Journal of Immunology, "Interactions Between NKG2X Immunoreceptors and HLA-E Ligands Display Overlapping Affinities and Thermodynamics", 2005, vol. 174, No. 5, pp. 2878-2884.
Kärre, K et al., Nature, "Selective Rejection of H-2-Deficient Lymphoma Variants Suggests Alternative Immune Defence Strategy", 1986, vol. 319, Number , pp. 675-678.
Ludewig B et al., Immunological Reviews., "Role of Dendritic Cells in the Induction and Maintenance of Autoimmune Diseases", 1999, vol. 169, Number , pp. 45-54.
Moretta, A et al, Annual Review of Immunology, "Activating Receptors and Coreceptors Involved in Human Natural Killer Cell-Mediated Cytolysis", 2001, vol. 19, Number -, pp. 197-223.
Martin et al., Immunogenetics, "The Genomic Organization and Evolution of the Natural Killer Immunoglobulin-Like Receptor (KIR) Gene Cluster", 2000, vol. 51, Number -, pp. 268-280.
Miller et al., Blood, "Human Natural Killer Cells With Polyclonal Lectin and Immunoglobulinlike Receptors Develop From Single Hematopoietic Stem Cells With Preferential Expression of NKG2A and KIR2DL2/L3/S2", 2001, vol. 98, No. 3, pp. 705-713.
Miller et al., Journal of Immunology, "Analysis of HLA-E Peptide-Binding Specificity and Contact Residues in Bound Peptide Required for Recognition by CD94/NKG2", 2003, vol. 171, Number , pp. 1369-1375.
Moretta A et al., Current Opinion in Immunology, "HLA Class I Specific Inhibitory Receptors", 1997, vol. 9, Number -, pp. 694-701.
Moretta L et al., The EMBO Journal, "Unravelling Natural Killer Cell Function: Triggering and Inhibitory Human NK Receptors", 2004, vol. 23, Number , pp. 255-259.
Ohlen C et al., Science, "Prevention of Allogeneic Bone Marrow Graft Rejection by H-2 Transgene in Donor Mice", 1989, vol. 246, Number , pp. 666-668.
Olszewski A j et al., Science STKE, "Empowering Targeted Therapy: Lessons From RITUXIMAB", 2004, vol. 241, Number , pp. 1-6.
Coupel et al., Blood, vol. 109, pp. 2806-2814 (2007).
Derre et al., Journal of Immunology, vol. 177, pp. 3100-3107 (2006).
Vance et al., Journal of Experimental Medicine, vol. 190, pp. 1801-1812 (1999).
Carter, P. et al., "Humanization of an Anit-P185 Antibody for Human Cancer Therapy," Preceedings of the National Academy of Science of the USA, 1992, vol. 89, No. 10, pp. 4285-4289.
Bagot et al., "Functional Inhibitory Receptors Expressed by a Cutaneous T-Cell Lymphoma-Specific Cytolytic Clonal T-Cell Population," Journal of Investigative Dermatology, 2000, vol. 115, No. 6, pp. 994-999.
Bagot et al., "CD4+ Cutaneous T-Cell Lymphoma Cells Express the p140-Killer Cell Immunoglobulin-like Receptor," Blood, 2001, vol. 97, No. 5, pp. 1388-1391.

Biassoni et al., "Molecular and Functional Characterization of NKG2D, NKp80, and NKG2C Triggering NK Cell Receptors in Rhesus and Cynomolgus Macaques: Monitoring of NK Cell Function During Simian HIV Infection," Journal of Immunology, 2005, vol. 174, pp. 5695-5705.
Carretero et al., "The CD94 and NKG2-A C-type Lectins Covalently Assemble to Form a Natural Killer Cell Inhibitory Receptor for HLA Class I Molecules," European Journal of Immunology, 1997, vol. 27, pp. 563-567.
Costa et al., "Differential Disappearance of Inhibitory Natural Killer Cell Receptors during HAART and Possible Impairment of HIV-1-Specific CD8 Cytotoxic T Lymphocytes," AIDS, 2001, vol. 15, pp. 965-974.
Haedicke et al., "Expression of CD94/NKG2A and Killer Immunoglobulin-Like Receptors in NK Cells and a Subset of Extranodal Cytotoxic T-cell Lymphomas," Blood, 2000, vol. 95, No. 11, pp. 3628-3630.
Kamarashev et al., "Differential Expression of Cytotoxic Molecules and Killer Cell Inhibitory Receptors in CD8+ and CD56+ Cutaneous Lymphomas," American Journal of Pathology, 2001, vol. 158, No. 5, pp. 1593-1598.
Le Bouteiller et al., "Engagement of CD160 Receptor by HLA-C is a Triggering Mechanism used by Circulating Natural Killer (NK) Cells to Mediate Cytotoxicity," Proceedings of the National Academy of Sciences in the USA, 2002, vol. 99, No. 26, pp. 16963-16968.
Mavilio et al., "Identification of NKG2A and NKp80 as Specific Natural Killer Cell Markers in Rhesus and Pigtailed Monkeys," Blood, 2005, vol. 106, No. 5, pp. 1718-1725.
Mingari et al., "HLA Class I-specific Inhibitory Receptors in Human T Lymphocytes: Interleukin 15-induced Expression of CD94/NKG2A in Superantigen- or Alloantigen- activated CD8+ T Cells," Proceedings of the National Academy of Sciences of the USA, 1998, vol. 95, pp. 1172-1177.
Ponte, et al., "Inhibitory Receptors Sensing HLA-G1 Molecules in Pregnancy: Decidua-associated Natural Killer Cells Express LIR-1 and CD94/NKG2A and Acquire p49, and HLA-G1-Specific Receptor," Proceedings of the National Academy of Sciences of the USA, 1999, vol. 96, pp. 5674-5679.
Sivori et al., "CD94 Functions as a Natural Killer Cell Inhibitory Receptor for Different HLA Class I Alleles: Identification of the Inhibitory Form of CD94 by the Use of Novel Monoclonal Antibodies," European Journal of Immunology, 1996, vol. 26, pp. 2487-2492.
Sivori et al., "p46, a Novel Natural Killer Cell-specific Surface Molecule that Mediates Cell Activation," Journal of Experimental Medicine, 1997, vol. 186, No. 7, pp. 1129-1136.
Vacca et al., "Analysis of Natural Killer Cells Isolated from Human Decidua: Evidence that 2B4 (CD244) Functions as an Inhibitory Receptor and Blocks NK-cell Function," Blood, 2006, vol. 108, No. 13, pp. 4078-4085.
Vitale et al., "The Leukocyte Ig-like Receptor (LIR)-1 for the Cytomegalovirous UL18 Protein Displays a Broad Specificity for Different HLA Class I Alleles: Analysis of LIR-1+ NK Cell Clones," International Immunology, 1999, vol. 11, No. 1, pp. 29-35.
Voss et al., "Participation of the CD94 Receptor Complex in Costimulation of Human Natural Killer Cells," Journal of Immunology, 1998, vol. 160, pp. 1618-1626.
Zimmer et al., "Activity and Phenotype of Natural Killer Cells in Peptide Transporter (TAP)-deficient Patients (Type I Bare Lymphocyte Syndrome)," Journal of Experimental Medicine, 1998, vol. 187, No. 1, pp. 117-122.
Castriconi et al., "Shaping of Adaptive Immunity by Innate Interactions," C.R. Biologies, 2004, vol. 327, pp. 533-537.
Guma et al., "Imprint of Human Cytomegalovirus Infection on the NK Cell Receptor Repertoire," Blood, 2004, vol. 104, No. 12, pp. 3664-3671.
Gunturi et al., "The Role of CD94/NKG2 in Innate and Adaptive Immunity," Immunologic Research, 2004, vol. 30, No. 1, pp. 29-34.
Jinushi et al., "Negative Regulation of NK Cell Activities by Inhibitor Receptor CD94/NKG2A Leads to Altered NK Cell-Induced Modulation of Dendritic Cell Functions in Chronic Hepatitis C Virus Infection," The Journal of Immunology, 2004, vol. 173, pp. 6072-6081.

(56) References Cited

OTHER PUBLICATIONS

Llano et al., "Differential Effects of US2, US6, and US11 Human Ctyomegalovirus Proteins on HLA Class Ia and HLA-E Expression: Impact on Target Susceptibility to NK Cell Subsets," European Journal of Immunology, 2003, vol. 33, pp. 2744-2754.

Riteau et al., "HLA-G1 Co-Expression Boosts the HLA Class I-Mediated NK Lysis Inhibition," International Immunology, 2001, vol. 13, No. 2, pp. 193-201.

Ward et al., HLA-C and HLA-E Reduce Antibody-Dependent Natural Killer Cell-Mediated Cyotoxicity of HIV-Infected Primary T Cell Blasts, AIDS, 2004, vol. 18, pp. 1769-1779.

Pedersen et al., "Differential Expression of Inhibitory or Activating CD94/NKG2 Subtypes on MART-1-Reactive T Cells in Vitiligo Versus Melanoma: A Case Report," J. Invest. Derm., 2002, vol. 118, pp. 595-599.

Wu M Anna et al., "Multimerization of a chimeric anti-CD20 single-chain Fv-Fc fusion protein is mediated through variable domain exchange," Prot. Engin., 2001, vol. 14, pp. 1025-1033.

Author Guide, Blood, pp. 1-19, Aug. 30, 2010.

Instructions to Authors, European Journal of Immunology, pp. 1-6, 2009.

Gavilondo et al., "Antibody Engineering at the Millennium," Biotechniques, 2000, vol. 29, No. 1, pp. 128-145.

Moretta et al., Identification of Four Subsets of Human CD3− CD16+ Natural Killer (NK) Cells by the Expression of Clonally Distributed Functional Surface Molecules: Correlation between Subset Assignment of NK Clones and Ability to Mediate Specific Alloantigen Recognition, J. Exp. Med., 1990, vol. 172, pp. 1589-1598.

Cleland et al., "The Development of Stable Protein Formulations: A Close Look at Protein Aggregation, Deamidation, and Oxidation," Critical Reviews in Therapeutic Drug Carrier Systems, 1993, vol. 10, No. 4, pp. 307-377.

Sablitzky et al., "Molecular Basis of an Isogenic Anti-Idiotypic Response," The EMBO Journal, 1984, vol. 3, No. 12, pp. 3005-3012.

Casset et al., Biochemical and Biophysical Research Communications, "A Peptide Mimetic of an Anti-CD4 Monoclonal Antibody by Rational Design", 2003, vol. 307, pp. 198-205.

Chen et al., Journal of Molecular Biology., "Selection and Analysis of an Optimized Anti-VEGF Antibody: Crystal Structure of an Affinity-Matured FAB in Complex With Antigen", 1999, vol. 293, pp. 865-881.

De Pascalis et al., Journal of Immunology, "Grafting of "Abbreviated" Complementarity-Determining Regions Containing Specificity-Determining Residues Essential for Ligand Contact to Engineer a Less Immunogenic Humanized Monoclonal Antibody", 2002, vol. 169, pp. 3076-3084.

Gonzales Noreen E et al, Tumor Biology, "Minimizing the Immunogenicity of Antibodies for Clinical Application", 2005, vol. 26, No. 1, pp. 31-43.

Holm et al., Molecular Immunology, "Functional Mapping and Single Chain Construction of the Anti-Cytokeratin 8 Monoclonal Antibody TS1", 2007, vol. 44, pp. 1075-1084.

Kashmiri et al., Methods, "SDR Grafting—A New Approach to Antibody Humanization", 2005, vol. 36, No. 1, pp. 25-34.

Kumar et al., Journal of Biological Chemistry, "Molecular Cloning and Expression of the FABS of Human Autoantibodies in *Escherichia coli*", 2000, vol. 275, pp. 35129-35136.

MacCallum et al., Journal of Molecular Biology., "Antibody-Antigen Interactions: Contact Analysis and Binding Site Topography", 1996, vol. 262, pp. 732-745.

Rudikoff et al., Proceedings of the National Academy of Sciences of the USA, "Single Amino Acid Substitution Altering Antigen-Binding Specificity", 1982, vol. 79, pp. 1979-1983.

Smith-Gill et al., Journal of Immunology, "Contributions of Immunoglobulin Heavy and Light Chains to Antibody Specificity for Lysozyme and Two Haptens", 1987, vol. 139, pp. 4135-4144.

Song et al., Biochemical and Biophysical Research Communications, "Light Chain of Natural Antibody Plays a Dominant Role in Proten Antigen Binding", 2000, vol. 268, pp. 390-394.

Vajdos et al., Journal of Molecular Biology., "Comprehensive Functional Maps of the Antigenbiding Site of an Anti-ERBB2 Antibody Obtained With Shotgun Scanning Mutagenesis", 2002, vol. 320, pp. 415-428.

Ward et al., Nature, "Binding Activities of a Repertoire of Single Immunoglobulin Variable Domains Secreted From *Escherichia coli*", 1989, vol. 341, pp. 544-546.

Wu H. et al., Journal of Molecular Biology, "Humanization of a Murine Monoclonal Antibody by Simultaneous Optimization of Framework and CDR Residues", 1999, vol. 294, No. 1, pp. 151-162.

Gessner et al., "The IgG Fc receptor family," 1998, Ann Hematol, vol. 76, pp. 231-248.

Reddy et al., "Elimination of Fc Receptor-Dependent Effector Functions of a Modified IgG4 Monoclonal Antibody to Human CD4," 2000, J. Immunol, vol. 164, pp. 1925-1933.

Yokoyama et al., "Immune functions encoded by the natural killer gene complex," 2003, Nature Rev Immunol, vol. 3, pp. 304-316.

Petrie, E. J., et al. CD94-NKG2A recognition of human leukocyte antigen (HLA)-E bound to an HLA class I leader sequence (2008), J. Exp. Med. 205; 725-735.

Pridgeon, C. et al. "Natural killer cells in the synovial fluid of rheumatoid arthritis patients exhibit a CD56bright,CD94bright,CD158negative phenotype," *Rheumatology*, Apr. 16, 2003, pp. 870-878, vol. 42.

Cooper, M. A. et al. "NK cell and DC interactions," *Trends in Immunology*, Jan. 2004, pp. 47-52, vol. 25, No. 1.

Teixeira De Matos, C. et al. "Activating and inhibitory receptors on synovial fluid natural killer cells of arthritis patients: role of CD94/NKG2A in control of cytokine secretion," *Immunology*, 2007, pp. 291-301, vol. 122.

Fauser, A. A. et al. "Guidelines for Anti-emetic Therapy: Acute Emesis" *Eur. J Canc.*, 1999, pp. 361-370, vol. 35. No. 3.

Leavenworth, J.W. et al. "Mobilization of natural killer cells inhibits development of collagen-induced arthritis," *PNAS*, Aug. 30, 2011, pp. 14584-14589, vol. 108, No. 35.

Park, K.S. et al. "Inhibitory NKG2A and activating NKG2D and NKG2C natural killer cell receptor genes: susceptibility for rheumatoid arthritis," *Tissue Antigens*, 2008, pp. 342-346, vol. 72.

D'Andrea, A. et al. "Regulation of T cell Lymphokine Production by killer Cell Inhibitory Receptor Recognition of Self HLA Class I Alleles," *J. Exp. Med.*, Aug. 1996, pp. 789-794, vol. 184.

Lu, L. et al. "Regulation of Activated CD4+ T Cells by NK Cells via the Qa-1-NKG2A Inhibitory Pathway," *Immunity*, May 2007, pp. 593-604, vol. 26.

Pende, D. et al. "HLA-G recognition by human natural killer cells. Involvement of CD94 both as inhibitory and as activating receptor complex," *Eur. J. Immunol.*, 1997, pp. 1875-1880, vol. 27.

Perez-Villar, J. J. et al. "The CD94/NKG2-A Inhibitory Receptor Complex is Involved in Natural Killer Cell-Mediated Recognition of Cells Expressing HLA-G1," *The Journal of Immunology.*, Mar. 14, 1997, pp. 5736-5743, vol. 158.

Presta, L.G. "Engineering of therapeutic antibodies to minimize immunogenicity and optimize function," *Advanced Drug Delivery Reviews*, 2006, pp. 640-656, vol. 58, No. 5-6.

Vance, R. E. et al. "Implications of CD94 deficiency and monoallelic NKG2A expression for natural killer cell development and repertoire formation," *PNAS*, Jan. 22, 2002, pp. 868-873, vol. 99, No. 2.

Zhang, A. L. et al. "Natural killer cells trigger differentiation of monocytes into dendritic cells," *Blood*, Oct. 1, 2007, pp. 2484-2493. vol. 110, No. 7.

Gooden, M. et al., "HLA-E expression by gynecological cancers restrains tumor-infiltrating CD8$^+$ T lymphocytes," *PNAS*, Jun. 28, 2011, pp. 10656-10661, vol. 108, No. 26.

Gooden, M. et al., "Infiltrating CTLs are bothered by HLA-E on tumors," *OncoImmunology*, 2012, pp. 92-93, vol. 1, No. 1.

Ishigami, S. et al., "Human Leukocyte Antigen (HLA)-E and HLA-F Expression in Gastric Cancer," *Anticancer Research*, 2015, pp. 2279-2286, vol. 35.

Nguyen, S. et al., "HLA-E upregulation on IFN-γ-activated AML blasts impairs CD94/NKG2A-dependent NK cytolysis after haplo-mismatched hematopoietic SCT," *Bone Marrow Transplantation*, 2009, pp. 693-699, vol. 43.

(56) References Cited

OTHER PUBLICATIONS

Sola, C. et al., "Anti-tumoral efficacy of therapeutic human anti-KIR antibody (lirilumab)," #493, *Innate Pharma, AACR Annual Meeting*, 2013, p. 1.

Veuillen, C. et al., "Primary B-CLL Resistance to NK Cell Cytotoxicity can be Overcome In Vitro and In Vivo by Priming NK Cells and Monoclonal Antibody Therapy," *J Clin Immunol*, 2012, pp. 632-646, vol. 32.

Yazdi, M.T. et al., "The positive prognostic effect of stromal CD8+ tumor-infiltrating T cells is restrained by the expression of HLA-E in non-small cell lung carcinoma," *Oncotarget*, Dec. 2, 2015, pp. 3477-3488, vol. 7, No. 3.

* cited by examiner

A
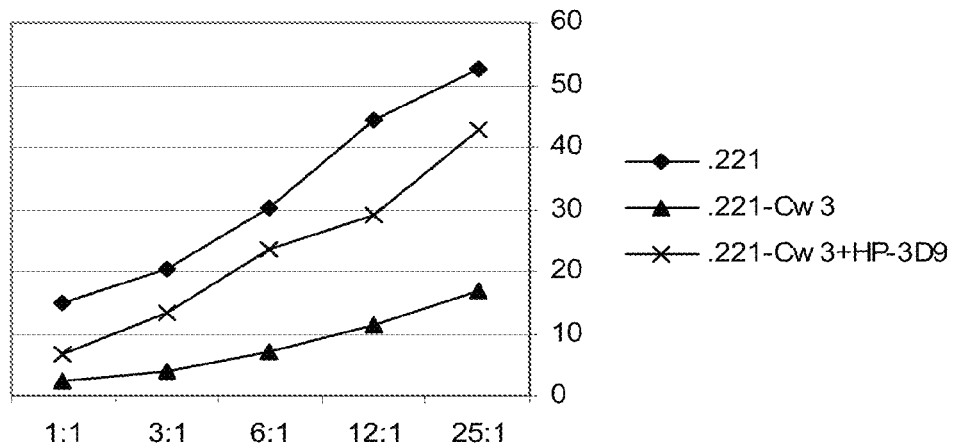
B
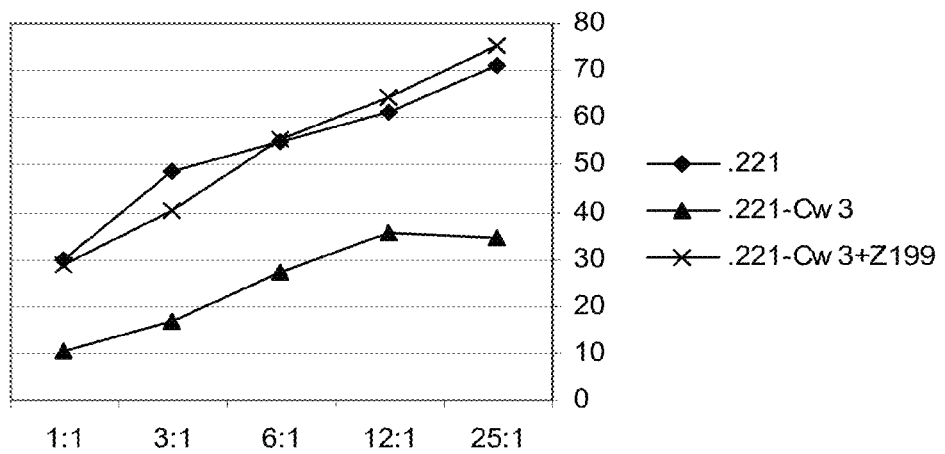
Fig. 1

```
Light Chain
         1         2         3          4         5         6
12345678901234567890123 4567ABCDEF8901234 5678901234567890 1234567890
QIVLTQSPALMSASPGEKVTMTCSASS    SVS YIYWYQQKPRSSPKPWIYLTSNLASGVPA
EIVLTQSPATLSLSPGERATLSCRASQ    SVSSYLAWYQQKPGQAPRLLIYDASNRASGIPA
EIVLTQSPATLSLSPGERATLSCSASS    SVSSYIYWYQQKPGQAPRLLIYLTSNLASGIPA 7         8         9         10
1234567890123456789012345678901 2345AB67890123456789  <- The Kabat Scheme
RFSGSGSGTSYSLTISSMEAEDAATYYCQQWSGNP   YTFGGGTKLEIKR  Z199 VL
RFSGSGSGTDFTLTISSLEPEDFAVYYCQQRSNWP   YTFGQGTKLEIK   VKIII_L6/JK2
RFSGSGSGTDFTLTISSLEPEDFAVYYCQQWSGNP   YTFGQGTKLEIK   humZ199 VL Heavy Chain
         1         2         3          4         5         6
1234567890123456789012 3456789012345AB6 7890123456789 012ABC34567890
EVQLVESGGGLVKPGGSLKLSCAASGFTFSSYAMS    WVRQSPEKRLEWVAEISS   GGSYTYYP
EVQLVESGGGLVKPGGSLRLSCAASGFTFSSYSMN    WVRQAPGKGLEWVSSISS   SSYIYYS  VH3_21
EVQLVESGGGLVKPGGSLRLSCAASGFTFSSYAMS    WVRQAPGKGLEWVSEISS   GGSYTYYA 7         8         9         10         11
1234567890123456789012ABC34567890123 4567890ABCDEFGHIJK1234567890  <- Kabat
DTVTGRFTISRDNAKNTLYLEISSLRSEDTAMYYCTRHGDYPRFF       DVWGAGTTVTVSS  Z199 VH
DSVKGRFTISRDNAKNSLYLQMNSLRAEDTAVYYCR//XYSSS        DVWGQGTTVTVSS  VH3_21/JH3
DSVKGRFTISRDNAKNSLYLQMNSLRAEDTAVYYCARHGDYPRFF       DVWGQGTTVTVSS  humZ199 VH
```

Fig. 4

```
Light Chain
         1         2         3           4         5         6
12345678901234567890123456 7ABCDEF 890123456789012345678901234567890
QIVLTQSPALMSASPGEKVTMTCSASS       SVS   YIYWYQQKPRSSPKPWIYLTSNLASGVPA
EIVLTQSPATLSLSPGERATLSCRASQ       SVSSYLAWYQQKPGQAPRLLIYDASNRATGIPA
EIVLTQSPATLSLSPGERATLSCSASS       SVSSYIYWYQQKPGQAPRLLIYLTSNLASGIPA
--------------------------*-**---------*-*-*------------------**-***-*----

7         8         9         10
12345678901234567890123456789012345AB67890123456789  <- The Kabat Scheme
RFSGSGSGTSYSLTISSMEAEDAATYYCQQWSGNP YTFGGGTKLEIKR    Z199 VL
RFSGSGSGTDFTLTISSLEPEDFAVYYCQQRSNWP YTFGQGTKLEIK     VKIII_L6/JK2
RFSGSGSGTDFTLTISSLEPEDFAVYYCQQWSGNP YTFGQGTKLEIK     humZ199 VL
---------------------------*-**---------------

Heavy Chain
         1         2         3         4         5         6
12345678901234567890123456789012345AB67890123456789012ABC34567890
EVQLVESGGGLVKPGGSLKLSCAASGFTFSSYAMS   WVRQSPEKRLEWVAEISS   GGSYTYYP  Z199 VH
EVQLVESGGGLVKPGGSLRLSCAASGFTFSSYSMN   WVRQAPGKGLEWVSSISS   SSSYIYYA  VH3_21
EVQLVESGGGLVKPGGSLRLSCAASGFTFSSYAMS   WVRQAPGKGLEWVSEISS   GGSYTYYA  humZ199 VH
------------------*-**----------------------------***--

7         8         9         10              11
1234567890123456789012ABC345678901234567890ABCDEFGHIJK1234567890 <- Kabat
DTVTGRFTISRDNAKNTLYLEISSLRSEDTAMYYCTRHGDYPRFF         DVWGAGTTVTVSS  Z199. VH
DSVKGRFTISRDNAKNSLYLQMNSLRAEDTAVYYCAR//YYYYGM         DVWGQGTTVTVSS  VH3_21/JH3
DSVKGRFTISRDNAKNSLYLQMNSLRAEDTAVYYCARHGDYPRFF         DVWGQGTTVTVSS  humZ199 VH
------------------------------------***----------- --*-----------
```

Fig. 7

```
                        10        11        12        13        14        15
              4567890123456789012345678901234567890123456789012345678901 23
NKG2A_HUMAN   PSTLIQRHNNSSLNTRTQKARHCGHCPEEWITYSNSCYYIGKERRTWEESLLACTSKNSS
NKG2C_HUMAN   --IPFLEQNNSSPNTRTQKARHCGHCPEEWITYSNSCYYIGKERRTWEESLLACTSKNSS
                : :**** *****************************************  ******

16        17        18        19        20        21
              456789012345678901234567890123456789012345678901234567890123
NKG2A_HUMAN   LLSIDNEEEMKFLSIISPSSWIGVFRNSSHHPWVTMNGLAFKHEIKDSDNAELNCAVLQV
NKG2C_HUMAN   LLSIDNEEEMKFLASILPSSWIGVFRNSSHHPWVTINGLAFKHKIKDSDNAELNCAVLQV
              ************: * ******************:******:*****************

22        23
              45678901234567890123
NKG2A_HUMAN   NRLKSAQCGSSIIYHCKHKL
NKG2C_HUMAN   NRLKSAQCGSSMIYHCKHKL
              ***********:********
```

Fig. 10

HUMANIZED ANTI-HUMAN NKG2A MONOCLONAL ANTIBODY

CROSS-REFERENCE TO RELATED APPLICATIONS

This application is a divisional of U.S. Ser. No. 12/811,990, filed Nov. 19, 2010, which is a national stage application of International Patent Application PCT/EP2009/050795 (published as WO 2009/092805), filed Jan. 23, 2009, which claimed priority of European Patent Application 08150601.6, filed Jan. 24, 2008, which claims priority under 35 U.S.C. §119 of U.S. Provisional Application 61/025,923, filed Feb. 4, 2008.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SeqListing", created on Jul. 27, 2014. The Sequence Listing is made up of 12 kilobytes, and the information contained in the attached "SeqListing" is identical to the information in the specification as originally filed. No new matter is added.

FIELD OF THE INVENTION

The present invention relates to non-competitive antagonists of CD94/NKG2A receptor, including certain anti-NKG2A antibodies, in particular humanized versions of murine anti-NKG2A antibody Z199, as well as methods of producing and using such antibodies.

BACKGROUND OF THE INVENTION

CD94/NKG2A is an inhibitory receptor found on subsets of natural killer cells (NK cells), Natural Killer T cells (NKT cells) and T cells (α/β and γ/δ). CD94/NKG2A restricts cytokine release and cytotoxic responses of aforementioned lymphocytes towards cells expressing the CD94/NKG2A-ligand HLA-E (see, e.g., WO99/28748). HLA-E has also been found to be secreted in soluble form by certain tumor cells (Derre et al., J Immunol 2006; 177:3100-7) and activated endothelial cells (Coupe) et al., Blood 2007; 109:2806-14). Antibodies that inhibit CD94/NKG2A signalling may increase the cytokine release and cytolytic activity of lymphocytes towards HLA-E positive target cells, such as responses of CD94/NKG2A-positive tumor-specific T-cells towards HLA-E expressing tumor cells, or NK responses towards virally infected cells. Therefore, therapeutic antibodies that inhibit CD94/NKG2A but that do not provoke the killing of CD94/NKG2A-expressing cells (i.e. non-depleting antibodies), may induce control of tumor-growth in cancer patients.

In addition, certain lymphomas such as, e.g., NK-lymphomas, are characterized by CD94/NKG2A expression. In such patients, therapeutic antibodies that target and kill CD94/NKG2A-expressing cells (i.e. depleting antibodies) may be able to eradicate tumor cells via antibody-dependent cellular cytotoxicity (ADCC) or complement-dependent cytotoxicity (CDC). Anti-NKG2A antibodies have also been suggested for use in treating autoimmune or inflammatory diseases (see, e.g., US20030095965, WO2006070286).

Various antibodies against NKG2A have been described in the art. For example, Sivori et al. (Eur J Immunol 1996; 26:2487-92) refers to the murine anti-NKG2A antibody Z270; Carretero et al. (Eur J Immunol 1997; 27:563-7) describes murine anti-NKG2A antibody Z199 (now commercially available via Beckman Coulter, Inc., Product No. IM2750, USA); Vance et al. (J Exp Med 1999; 190: 1801-12) refers to rat anti-murine NKG2-antibody 20D5 (now commercially available via BD Biosciences Pharmingen, Catalog No. 550518, USA); and U.S. patent application publication 20030095965 describes murine antibody 3S9, which purportedly binds to NKG2A, NKG2C and NKG2E.

Currently available anti-CD94/NKG2A antibodies are of non-human origin, which makes them unsuitable for most therapeutic applications in humans due to their immunogenicity. Accordingly, there is a need for anti-CD94/NKG2A antibodies that are suitable for treatment of human patients.

SUMMARY OF THE INVENTION

The present invention provides NKG2A binding agents, such as anti-NKG2A antibodies, as well as compositions comprising such agents, and methods of producing and using such agents. The agents are typically non-competitive antagonists of the human CD94/NKG2A receptor, and reduce the inhibitory activity of the receptor without blocking binding of its ligand, HLA-E. In one embodiment, the agent is antibody which binds with a significantly higher affinity to NKG2A than to NKG2C, and binds a segment of NKG2A comprising residues P94-N107 and/or M189-E197, or to both segments. In an additional or alternative embodiment, the agent competes with the murine anti-NKG2A antibody Z199 in binding to CD94/NKG2A. The agent can be, e.g., a human or humanized anti-NKG2A antibody.

In one embodiment, the humanized antibody is a humanized version of Z199. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided. In one aspect, the invention provides humanized antibodies in which at least a portion of a Z199 Kabat CDR is identical to the corresponding portion in the human acceptor sequence. In one embodiment, the human framework sequence comprises at least one back-mutation, such as e.g. one, two, three, four, five or six back-mutation. In another embodiment, the human framework sequence of the variable light (VL) domain comprises a single back-mutation.

In other aspects, the invention provides for pharmaceutical compositions comprising such agents and a carrier, and for conjugates comprising such agents conjugated to e.g. a cytotoxic or detectable agent.

In other aspects, the invention provides for nucleic acids and vectors encoding such agents, and host cells containing such nucleic acids and/or vectors. Also provided for are recombinant methods of producing the agents by culturing such host cells so that the nucleic acids are produced.

In other aspects, the invention provides for articles of manufacture comprising a container comprising such agents and instructions directing a user to treat a disorder such as cancer or a viral disease in a patient. Optionally, the article may comprise another container containing another agent, wherein the instructions direct the user to treat the disorder with the antibody in combination with the agent.

The invention also provides for methods of using the agents of the invention in the treatment of disorders such as cancer, a viral disease, an inflammatory disorder or an autoimmune disorder in a patient, optionally in conjunction with another anti-cancer, anti-viral disease agent, or anti-inflammatory agent.

DESCRIPTION OF THE DRAWINGS

FIGS. 1A-1B show the results of a Cr-51 release assay evaluating the ability of CD94/NKG2A-expressing NKL cells to kill target cells expressing or lacking functional HLA-E, as well as the effect of murine antibodies HP-3D9 (A) (anti-CD94) or Z199 (B) (anti-NKG2A) on the killing of HLA-E expressing target cells. The NKL cells efficiently killed Cr-51-labeled target cells which lacked functional HLA-E, whereas target cells expressing functional HLA-E were less efficiently killed. When NKL cells were pre-incubated with Z199, target cells expressing HLA-E were equally well killed as target cells lacking HLA-E, confirming that Z199 functionally inhibits CD94/NKG2A.

FIG. 4 shows the sequence analysis made for humanization of the VL (SEQ ID NO:2) and VH (SEQ ID NO:4) sequences of Z199. In the first line showing the residue numbering according to the Kabat scheme, the mask is shown with underlining, and the Kabat CDRs are shown in bold. In the germline sequences, the mouse/human germline differences are given with grey background (VKIII_L6/JK2: SEQ ID NO:12; VH3_21/JH3: SEQ ID NO:14). The resulting sequences for the VL (SEQ ID NO:13) and VH (SEQ ID NO:15) regions of humanized Z199 (humZ199) are given with the potential back mutation residues as human in bold and underlined.

FIG. 7 shows the position of Ala-mutations made in Z199 VL and VH sequences, as indicated by asterisks. See FIG. 4 for sequence identifiers.

FIG. 10 shows mapping of exposed residues (underlined) onto the alignment of NKG2A (SEQ ID NO:11) and NKG2C (SEQ ID NO:16). Residue numbering from the NKG2A sequence was used. Conserved residues are marked by *.

DEFINITIONS

Figure 2:
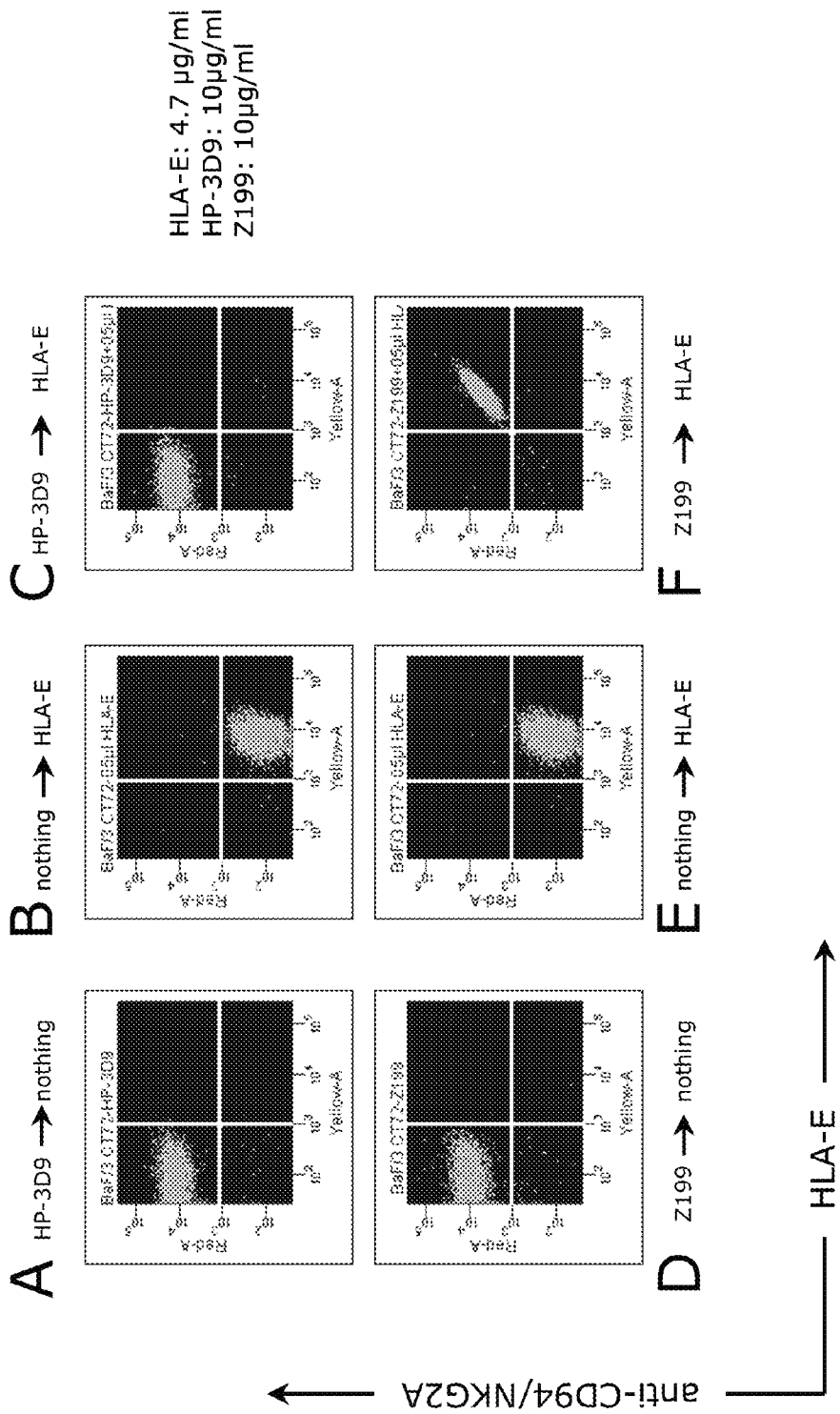
FIG. 2 shows a Biacore experiment where a single-chain CD94/NKG2A Fc (scCD94-NKG2A-Fc) construct pre-incubated with HLA-E tetramers could bind Z199, whereas HP-3D9 was prevented from binding.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity (e.g., binding to human CD94/NKG2A). Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).).

An "antibody fragment" comprises a portion of a full-length antibody, preferably antigen-binding or variable regions thereof and include synthetic and semi-synthetic antibody-derived molecules. Examples of antibody fragments include Fab, Fab', F(ab)2, F(ab')2, F(ab)3, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136; WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like, e.g., for linking the antibody to a second molecule. This includes, but is not limited to, PEGylated antibodies, cysteine-PEGylated antibodies, and variants thereof.

An "immunoconjugate" as used herein comprises an agent according to the invention such as an antibody derivative associated with or linked to a second agent, such as a cytotoxic agent, a detectable agent, etc.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen-binding. The hypervariable region generally comprises amino acid residues from a "complementarity-determining region" or "CDR" (residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991, supra) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917). Typically, the numbering of amino acid residues in this region is performed by the method described in Kabat et al., supra. Phrases such as "Kabat position", "Kabat residue", "using Kabat numbering", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. Unless otherwise indicated or contrary to context, the position of all amino acid residues in a VL or VH sequence described herein are according to Kabat.

"Framework region" or "FR" residues are those VH or VL residues other than the CDRs as herein defined.

A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98: Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An antibody having a "biological characteristic" of a reference antibody, (e.g., Z199), is one that possesses one or more of the biological characteristics of that antibody that distinguish it from other antibodies that bind to the same antigen (e.g. NKG2A). For example, an antibody with a biological characteristic of Z199 may block activation of NKG2A, and/or cross-compete with Z199 in binding the extracellular domain of NKG2A.

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence:

(SEQ ID NO: 11)
MDNQGVIYSDLNLPPNPKRQQRKPKGNKSSILATEQEITYAELNLQKASQ

DFQGNDKTYHCKDLPSAPEKLIVGILGIICLILMASVVTIVVIPSTLIQR

```
HNNSSLNTRTQKARHCGHCPEEWITYSNSCYYIGKERRTWEESLLACTSK

NSSLLSIDNEEEMKFLSIISPSSWIGVFRNSSHHPWVTMNGLAFKHEIKD

SDNAELNCAVLQVNRLKSAQCGSSIIYHCKHKL.
```

NKG2C (SEQ ID NO:16; OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present invention, "treatment" or "treating" refers to preventing, alleviating, ameliorating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

In the context of the present invention, "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "CD94/NKG2A positive lymphocyte" also includes immortal cell lines of lymphoid origin (e.g. NKL, NK-92).

In the context of the present invention, "reduces the inhibitory activity of human CD94/NKG2A receptor expressed on the surface of a CD94/NKG2A positive lymphocyte" refers to a process in which CD94/NKG2A is inhibited in its capacity to negatively affect intracellular processes leading to lymphocyte responses such as cytokine release and cytotoxic responses. This can be measured for example in a standard NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, preferably at least a 40% or 50% augmentation in lymphocyte cytotoxicity, or more preferably at least a 70% augmentation in NK cytotoxicity", and referring to the cytotoxicity assays described.

In the context of the present invention, "an agent that binds to human CD94/NKG2A receptor" refers to an agent with detectable binding to human CD94/NKG2A receptor using any standard assay where the agent is incubated in the presence of CD94/NKG2A or NKG2A and binding detected via, e.g., radiolabels, physical methods such as mass spectrometry, or direct or indirect fluorescent labels detected using, e.g., cytofluorometric analysis (e.g. FACScan). Any amount of binding above the amount seen with a control, non-specific agent indicates that the agent binds to the target.

In the context of the present invention, "Z199 antibody" is the murine anti-NKG2A antibody Z199 as described by Carretero et al. (Eur J Immunol 1997; 27:563-7), now commercially available via Beckman Coulter, Inc., Product No. IM2750, USA). Determination of the VH and VL sequences of Z199 is described in Example 2. Humanized versions of Z199 can be referred to as "humZ199", "huZ199", "hzZ199", or "hZ199" herein.

DESCRIPTION OF THE INVENTION

The present invention is based, in part, on the discovery that certain agents that bind the extra-cellular portion of human NKG2A are non-competitive antagonists, i.e., reduce the inhibitory activity of the CD94/NKG2A receptor without blocking HLA-E binding to the receptor. Preferred agents bind to the inhibitory CD94/NKG2A receptor with higher efficacy than to the activating CD94/NKG2C receptor. As shown herein, such agents can bind a segment of NKG2A (SEQ ID NO:11) comprising residues P94-N107, M189-E197, or both. The non-competitive CD94/NKG2A antagonists of the invention can be used as therapeutic agents in several types of diseases and disorders, such as, e.g., cancer, viral diseases, autoimmune diseases and/or inflammatory disorders. A non-competitive antagonist can advantageously be used for, e.g., therapeutic applications where soluble HLA-E is present.

Figure 3:
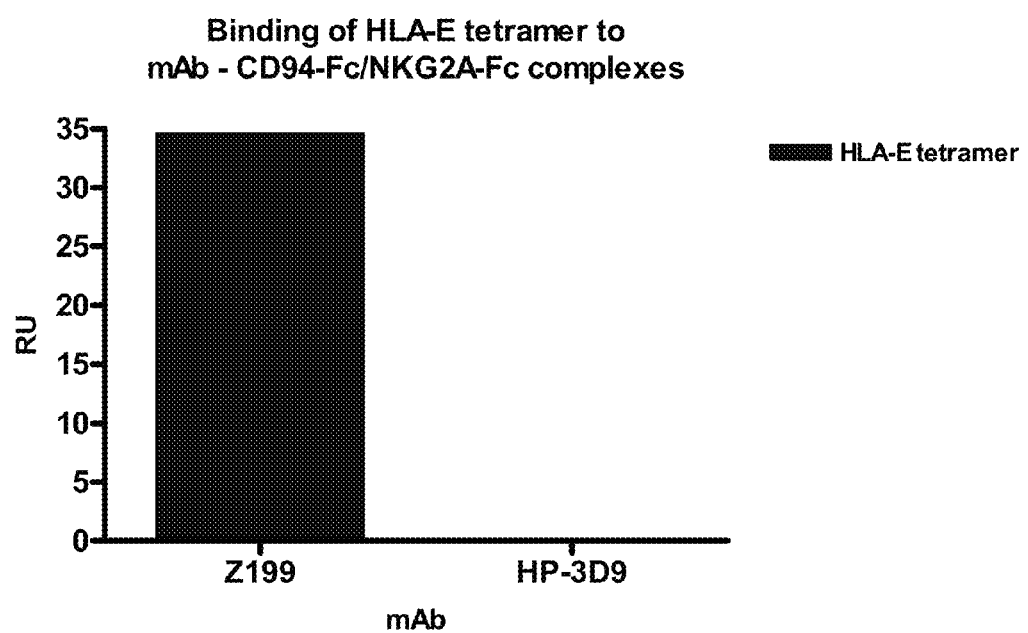
FIG. 3 shows that Ba/F3 cells over-expressing CD94/NKG2A bound HLA-E tetramers, HP-3D9, and Z199, as evaluated by flow-cytometry. When pre-incubated with Z199, Ba/F3-CD94/NKG2A cells could still bind HLA-E tetramers, but not when pre-incubated with HP-3D9.

One type of non-competitive antagonists described herein is anti-NKG2A antibodies, in particular antibodies suitable for treatment of human patients. Such an antibody can be a human antibody or a humanized version of a non-human (e.g., murine) antibody. Human or humanized antibodies competing with murine antibody Z199 in binding to human CD94/NKG2A are a particular aspect of the invention. In one embodiment, a human or humanized antibody that competes with Z199 in binding to CD94/NKG2A receptor binds a segment of NKG2A comprising residues P94-N107, M189-E197, or binds to both segments. For example, the antibody can bind an epitope comprising a residue selected from P94, S95, T96, L97, I98, Q99, R100, H101, L106, M189, or E197 of NKG2A. In another embodiment, the antibody binds the same epitope as Z199. As described in the Examples, Z199 was found to be a non-competitive antagonist of human CD94/NKG2A receptor expressed on lymphocytes, since Z199 inhibited the function of CD94/NKG2A (illustrated in FIG. 1), but did not affect HLA-E binding to CD94/NKG2A receptor (FIGS. 2 and 3). Z199 further bound to CD94/NKG2A receptor with a high specificity, with a KD at least a 100-fold lower than that of binding to CD94/NKG2C receptor.

In another aspect, the invention provides particular humanized antibodies that are humanized versions of Z199. Such antibodies are typically characterized by comprising key amino acid residues from Z199 CDRs in human framework sequences. For example, a humanized Z199 antibody can comprise Kabat residues Y32, L50, and P95 in the Z199 VL domain, and Kabat residues Y56, Y98 and P99 in the Z199 VH domain. In the Z199 VH and VL sequences, these correspond to amino acid residues Y31, L49, and P94 of the Z199 VL domain (SEQ ID NO:2), and amino acid residues Y57, Y102, and P103 of the Z199 VH domain (SEQ ID NO:4) at the Kabat positions corresponding to those in the Z199 CDRs.

The humanized Z199 antibody may further comprise one or more back-mutations in the human framework sequences, to, e.g., enhance affinity, stability, or other properties of the humanized antibody. Preferred back-mutations include those resulting in the humanized antibody comprising one or more of amino acid residues Q1, P45, W46, V57, and S69 of the Z199 VL domain sequence and/or one or more of amino acid residues A49, T78, and T97 of the Z199 VH domain sequence, preferably at least residue P45 of the Z199 VL domain sequence, preferably at Kabat positions corresponding to those in Z199 VH and VL domains. In one embodiment, the humanized Z199 antibody comprises at least amino acid residues 24-33, 49-55, and 88-96 of the Z199 VL domain sequence, and at least amino acid residues 31-35, 50-60 and 99-108 of the Z199 VH domain sequence, optionally also residues 62, 64, 66 of the Z199 VH domain sequence. The humanized antibody may also contain one or more amino acids inserted into the CDRs, particularly CDR_L1, such as, e.g., a serine (S) inserted between residues 30 and 31 of the Z199 VL domain.

In another aspect, the invention provides an isolated antibody binding human CD94/NKG2A receptor and comprising
(a) a CDR-L1 comprising SEQ ID NO:5;
(b) a CDR-L2 comprising SEQ ID NO:6;
(c) a CDR-L3 comprising SEQ ID NO:7;
(d) a CDR-H1 comprising SEQ ID NO:8;
(e) a CDR-H2 comprising SEQ ID NO:9;
(f) a CDR-H3 comprising SEQ ID NO:10;
(g) human framework sequences; and
(h) a proline (P) residue at Kabat position 46 of the VL domain.

The praline (P) residue at Kabat position 46 may exist naturally in the human VL framework sequence, or may be introduced by amino acid substitution or other modification of the sequence. In a specific embodiment, the antibody comprises a VL sequence comprising SEQ ID NO:13 with an L46P mutation, and a VH sequence comprising SEQ ID NO:15. The antibody may further comprise an IgG4 constant domain, with an optional S241P mutation to improve stability.

These and other aspects are described in more detail in the following sections and in the Examples.

Agents

The present invention relates to an agent that binds an extra-cellular portion of human CD94/NKG2A receptor, wherein the agent (a) reduces the inhibitory activity of human CD94/NKG2A receptor expressed on the surface of a CD94/NKG2A positive lymphocyte; and (b) is capable of binding CD94/NKG2A simultaneously with HLA-E, wherein the agent is not the Z199 antibody.

In an additional or alternative embodiment, the present invention relates to an agent that binds an extra-cellular portion of human CD94/NKG2A receptor, wherein the agent (a) reduces the inhibitory activity of human CD94/NKG2A receptor expressed on the surface of a CD94/NKG2A positive lymphocyte; and (b) does not compete with HLA-E in binding to CD94/NKG2A, wherein the agent is not an antibody comprising a light chain variable domain (VL) sequence comprising SEQ ID NO:2 and a heavy chain variable domain (VH) sequence comprising SEQ ID NO:4.

In one aspect of the invention, the CD94/NKG2A positive lymphocyte is selected from the group consisting of a NK cell, a cytotoxic T cell such as an α/β T cell or a γ/δ T cell, and NKT cells.

In one aspect of the invention, the agent is an antibody selected from a full-length antibody, an antibody fragment, and a synthetic or semi-synthetic antibody-derived molecule, which includes at least CDRs from an antibody which competes with the Z199 antibody for binding to CD94/NKG2A.

In one aspect of the invention, the agent is an antibody selected from a fully human antibody, a humanized antibody, and a chimeric antibody.

In one aspect of the invention, the agent is an antibody selected from an IgA, an IgD, an IgG, an IgE and an IgM antibody.

In one aspect of the invention, the agent is an antibody comprising a human constant domain selected from an IgG1, IgG2, IgG3 and IgG4 isotype.

In one aspect of the invention, the agent is a fragment of an antibody selected from IgA, an IgD, an IgG, an IgE and an IgM antibody.

In one aspect of the invention, the agent is a fragment of an antibody comprising a constant domain selected from IgG1, IgG2, IgG3 and IgG4.

In one aspect of the invention, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment.

In one aspect of the invention, the agent is a synthetic or semisynthetic antibody-derived molecule selected from a scFV, a dsFV, a minibody, a diabody, a triabody, a kappa body, an IgNAR; and a multispecific antibody.

The present invention thus concerns antibodies or other agents binding to NKG2A. In one aspect, the antibody is a humanized version of antibody Z199, which is a murine monoclonal antibody that binds to NKG2A with a KD at least 100-fold lower than to human NKG2C or NKG2E. Z199 can block the function of human CD94/NKG2A, and specifically induce killing of cells by CD94/NKG2A-restricted lymphocytes in a concentration-dependent fashion.

In one aspect of the invention, the agent reduces CD94/NKG2A-mediated inhibition of a CD94/NKG2A-expressing lymphocyte by interfering with CD94/NKG2A signalling by, e.g., preventing or inducing conformational changes in the CD94/NKG2A receptor, and/or affecting dimerization and/or clustering of the CD94/NKG2A receptor.

In one aspect of the invention, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10.000 fold lower than to NKG2C. In another aspect of the invention, the agent binds to an extracellular portion of NKG2A with a KD at least 100 fold lower than to NKG2C or NKG2E molecules. In a further preferred aspect, the agent binds to an extracellular portion of NKG2A with a KD at least 150, 200, 300, 400, or 10.000 fold lower than to NKG2C or NKG2E molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies of the invention may optionally bind NKG2B, which is an NKG2A splice variant forming an inhibitory receptor together with CD94.

In one aspect of the invention, the agent competes with antibody Z199 in binding to the extra-cellular portion of human CD94/NKG2A receptor. This can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with Z199. Alternatively, the binding of agents to cells is measured that either naturally express, or over-express (e.g. after transient or stable transfection), CD94/NKG2A receptor, and which have been pre-incubated with saturating doses of Z199.

In one aspect of the invention, the agent binds to the same, or essentially the same epitope as Z199 antibody.

In one aspect of the invention, the agent comprises CDR sequences derived from the Z199 VH and VL domains. In another aspect of the invention, the agent comprises amino acid substitutions, deletions, or insertions in the Z199 CDR sequences. In another aspect of the invention, the agent comprises back-mutations in the native murine CDR sequences such as a limited number of substitutions e.g. one, two, three, four, five, or six back-mutations in the Z199 CDR.

In one aspect of the invention, the agent comprises amino acid residues 31-35, 50-60, 62, 64, 66, and 99-108 of the Z199 variable-heavy ($V_H$) domain (SEQ ID NO: 4) and amino acid residues 24-33, 49-55, and 88-96 of Z199 variable-light ($V_L$) domain (SEQ ID NO: 2), optionally with one, two, three, four, or more amino acid substitutions.

In one aspect of the invention, the agent is a fully human or a humanized antibody comprising a proline at Kabat position 46 of the light chain.

In one aspect of the invention, the agent includes human framework regions selected from the group consisting of recombined germline sequences and associated somatic hypermutation.

In one aspect of the invention, the antibody comprises human VH3_21 and VKIII_L6 scaffold sequences, with JH3 and JK2 as germline J-segments, but in principle many other templates can be used such as VH3_21, VH3_23, VH3_11, VH3_07, VH3_48, VH3_30_3, VH3_64, VH3_30_5 (heavy chain) and VKIII_L6, VKI_L23, VKIII_A11, VKIII_A27, VKIII_L20, VKVI_A14, VKI_L23, VKI_L8, VKI_L15 (light Chain).

In one aspect of the invention, the agent is a fully human antibody which has been raised against the CD94/NKG2A epitope to which antibody Z199 binds, or raised against an anti-idiotypic antibody specifically binding the idiotype of Z199.

In one aspect of the invention, the agent comprises human framework sequences, a proline residue at position 46 and the following complementarity-determining regions (CDRs): a) a CDR-H1 comprising SEQ ID NO: 8; b) a CDR-H2 comprising SEQ ID NO: 9; c) a CDR-H3 comprising SEQ ID NO: 10; d) a CDR-L1 comprising SEQ ID NO: 5; e) a CDR-L2 comprising SEQ ID NO: 6; and f) a CDR-L3 comprising SEQ ID NO: 7.

In one aspect of the invention, the agent is in at least partially purified form.

In one aspect of the invention, the agent is in essentially isolated form.

The invention provides, e.g., humZ199 variants in which at least a portion of a VH CDR such as the CDR-H2 is identical to the corresponding portion of the human VH acceptor sequence, thus reducing the immunogenicity of the humanized antibody. For example, as shown in FIG. 4, residues Y58 to G65 in the humZ199 CDR-H2 are identical to the VH3_21 sequence. Such humanized variants can also be effective in potentiating the cytotoxicity of a CD94/NKG2A-expressing cytotoxic lymphocyte similar to the murine or a chimeric form of Z199. In other aspects, the invention provides antibodies having CDRs comprising certain antigen-binding residues corresponding to those in murine antibody Z199, and human framework sequences. For example, as shown in Example 4, Kabat residues Y32, L50, and P95 in the Z199 VL CDRs and Kabat residues Y56, Y98, and Y99 significantly contribute to antigen recognition. In one embodiment, an antibody according to the invention thus comprises at least some, preferably all of these residues.

Humanized Anti-NKG2A Antibodies

Methods for humanizing non-human antibodies have been described in the art. Generally, in a humanization process, nucleotides encoding the interaction-regions of a murine antibody can be cloned into a cDNA-vector encoding human IgG, which can be done such that a chimeric antibody is generated consisting of a human IgG backbone harboring amino acid residues from the murine CDRs. Such antibodies may exhibit a lower affinity, lower stability, or other undesired features in comparison with the original murine antibody, and may also be immunogenic. Therefore, individual amino acids in the chimeric Ab may need to be optimized to obtain a functional mAb of high quality for therapeutic applications in humans.

Typically, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al, Nature, 321: 522-525 (1986); Riechmann et al., Nature, 332: 323-327 (1988); Verhoeyen et al., Science, 239: 1534-1536 (1988)), by substituting hypervariable region sequences for the corresponding sequences of a human "acceptor" antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Another method for making humanized antibodies is described in U.S. patent application publication 2003/0017534, wherein humanized antibodies and antibody preparations are produced from transgenic non-human animals. The non-human animals are genetically engineered to contain one or more humanized immunoglobulin loci that are capable of undergoing gene rearrangement and gene conversion in the transgenic non-human animals to produce diversified humanized immunoglobulins.

The choice of human variable domains, both light and heavy, to be used in making the humanized antibodies is very important to reduce antigenicity. According to the so-called "best-fit" method, the sequence of the variable domain of a rodent antibody is screened against a library of known human variable-domain sequences or a library of human germline sequences. The human sequence that is closest to that of the rodent can then be accepted as the human framework region for the humanized antibody (Sims et al., J. Immunol. 1993; 151:2296 et seq.; Chothia et al, Chothia and Lesk, J. Mol. Biol 1987; 196:901-917). Another method uses a particular framework region derived from the consensus sequence of all human antibodies of a particular subgroup of light or heavy chains. The same framework may be used for several different humanized antibodies (Carter et al., PNAS USA, 1992; 89:4285 et seq.; Presta et al., J Immunol 1993; 151:2623 et seq.). Other methods designed to reduce the immunogenicity of the antibody molecule in a human patient include veneered antibodies (see, e.g., U.S. Pat. No. 6,797,492 and U.S. patent application publications 20020034765 and 20040253645) and antibodies that have been modified by T-cell epitope analysis and removal (see, e.g., U.S. patent application publications 20030153043 and U.S. Pat. No. 5,712,120).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The surprising finding that Z199 is a non-competitive CD94/NKG2A antagonist is shown in Example 1 and FIGS. 1, 2 and 3. HP-3D9 (anti-CD94)(FIG. 1A), Z199 (anti-NKG2A)(FIG. 1B) and Z270 (anti-NKG2A) all efficiently induced killing of HLA-E expressing target cells by CD94/NKG2A-restricted lymphocytes. However, while HP-3D9 and Z270 prevented the interaction between CD94/NKG2A and HLA-E, Z199 did not prevent this interaction. Further, humZ199, tested in the dose range 100 pg/ml to 1 µg/ml, was able to bind CD94/NKG2A-expressing cells pre-incubated with a saturating dose of HLA-E tetramers.

Z199 and humZ199 are therefore non-competitive CD94/NKG2A antagonists. While not limited to theory, it is possible that Z199 interferes with CD94/NKG2A signalling by, e.g., preventing or inducing conformational changes in the CD94/NKG2A receptor, and/or affecting dimerization and/or clustering of the CD94/NKG2A receptor.

In one aspect, an agent according to the invention is a non-competitive antagonist. In a further aspect, an agent according to the invention is a non-competitive antagonist having a different effect on the rate or amount of internalization of the CD94/NKG2A receptor, thus making more or fewer antigens available for binding by additional therapeutic agents and/or HLA-E. Agents that prevent the interaction between CD94/NKG2A receptor and HLA-E may lead to an increase in binding of HLA-E to other CD94/NKG2 receptors (e.g. CD94/NKG2C), which activation may cause unwanted biological responses triggered by these receptors (e.g. resulting in unwanted pro-inflammatory responses). In one aspect, an agent according to the invention blocks CD94/NKG2A receptor without increasing the potential of HLA-E to bind and trigger other CD94/NKG2 receptors, making unwanted side-effects caused by other CD94/NKG2 receptors less likely.

Figure 5:
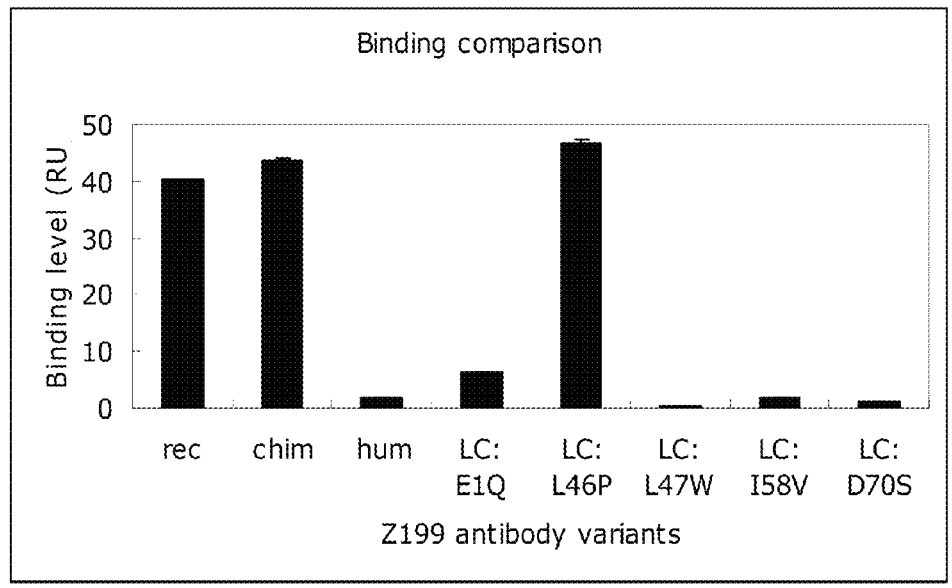
FIG. 5 shows the binding profiles in Biacore of humZ199 variants with back-mutations E1Q, L46P, L47W, I58V or D70S in the light chain. Whereas the recombinantly expressed parental murine antibody Z199 (rec) and chimeric Z199 with a human IgG4(S241P) portion (chim) efficiently bound scCD94/NKG2A-Fc, humanized Z199 without any backmutations (hum) had a very low capacity for binding scCD94-NKG2A-Fc. By contrast, a single backmutation L46P in the Z199 light chain restored the binding.
Figure 6:
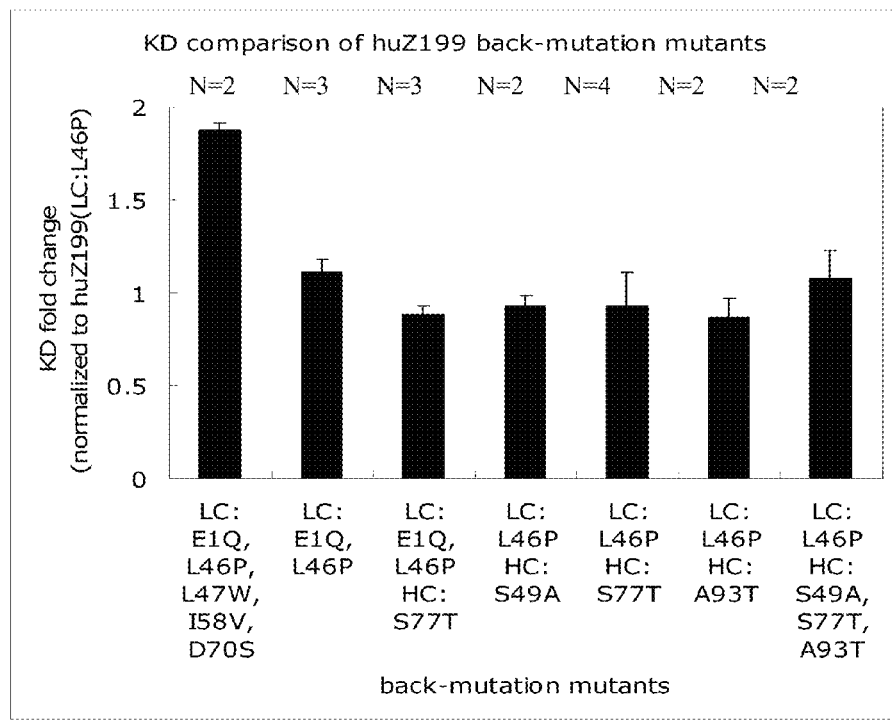
FIG. 6 shows affinity determination of humZ199 variants with selected back mutations combined with L46P in the light chain. The KD value of each mutant was normalized to that of humZ199 with an L46P mutation in the light chain (designated "huZ199(LC:L46P)" in the figure) to obtain the relative change in KD.

Example 2 describes the design of exemplary humanized anti-NKG2A antibodies and example 3 describes the Biacore analysis of humZ199 and back-mutation variants. Initially, humanized Z199 antibody was found not able to bind to the antigen. Therefore, back mutation was introduced to the light chain and heavy chain of humZ199. Interestingly, the back-mutation L46P in the light chain restored the ability of the antibody to recognize and bind to the antigen (FIG. 5). The affinity of this mutant was determined as 72 pM, which was in the same order of magnitude as chimeric Z199 (24 pM) (Table 1). Other back mutations in the light chain did not significantly enhance the affinity of the antibody when combined with L46P (FIG. 6).

Figure 9:
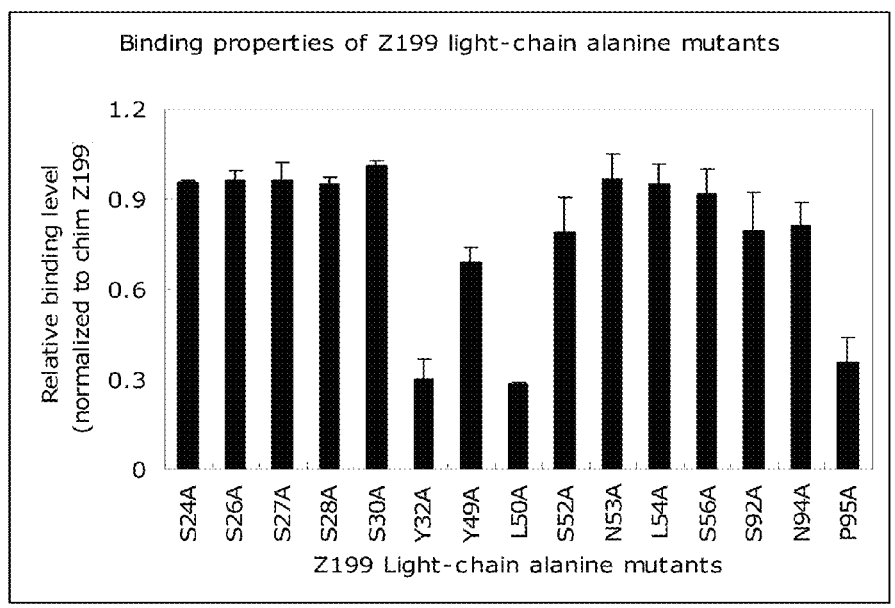
FIG. 9 shows the binding of Z199 with alanine mutations in the VL region to immobilized sc-CD94-NKG2A-Fc, normalized to the binding of chimZ199.

Example 4 shows identification of critical residues in the Z199 variable sequences by an alanine-scan. As compared to chimeric Z199, all ala-mutants tested showed a comparable binding profile at the two mAb concentrations used in the assay (2.5 nM and 5 nM), with the exception of Z199 variants where Kabat residues Y32, L50 or P95 in the chimeric Z199 light chain were substituted for an alanine, or where Kabat residues Y56, Y98 or P99 in the heavy chain were substituted for an alanine. Z199 light-chain alanine mutants Y32A, L50A, and P95A demonstrated antigen-binding abilities around 40%. The relative binding of light-chain mutant Y49A was between 60-80% (FIG. 9). Therefore, the Kabat residues Y32, L50, and P95 in the Z199 light chain significantly contributed to recognize the antigen whereas the Kabat residue Y49 in the light chain moderately affected the antigen-binding. Accordingly, the invention provides for humZ199 variants, which retain the Kabat residues Y32, L50 or P95 in the VL domain.

With respect to the numbering of amino acid residues, it should be noted that the variable domain of the murine Z199 light chain is one residue shorter than that of humZ199, lacking the residue corresponding to Kabat residue S31 in the humZ199 light chain sequence (FIGS. 4 and 7). Therefore, residues numbered according to Kabat as, e.g., Y32, L46, L50 and P95 in the humZ199 light chain sequence correspond to Kabat residues Y31, P45, L49 and P94 in the murine Z199 light chain sequence. However, the Kabat numbering shown in FIGS. 4 and 7 is used as a standard for Kabat numbering of all Z199 (murine or humanized, native or mutated, heavy or light chain) variable region residues referred to herein, unless otherwise indicated.

Figure 8:
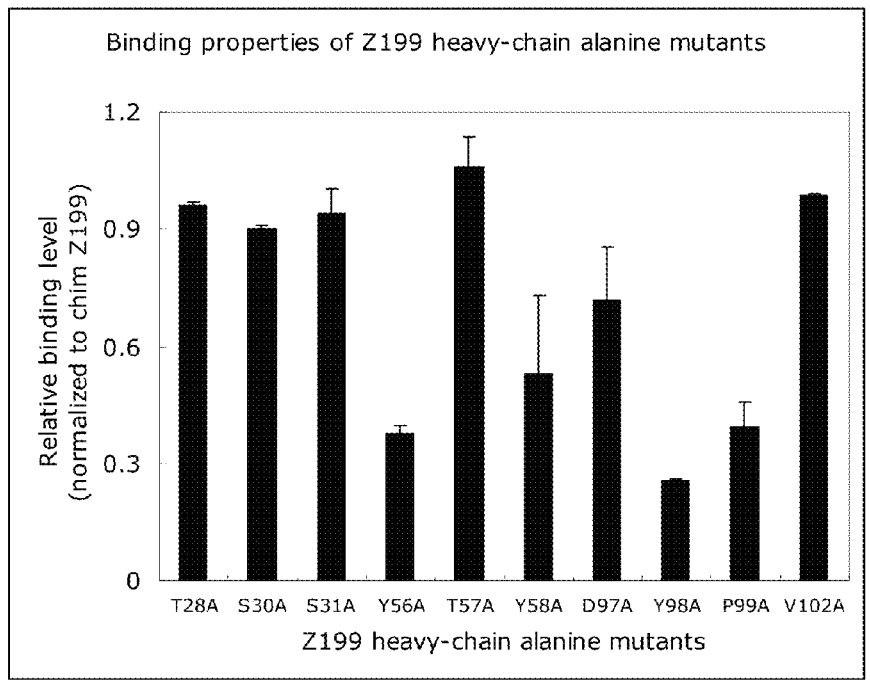
FIG. 8 shows the binding of Z199 with alanine mutations in the VH region to immobilized scCD94-NKG2A-Fc, normalized to the binding of chimZ199.

Z199 heavy-chain alanine mutants Y56A, Y98A, and P99A retained around 40% of the antigen-binding abilities whereas the relative binding of heavy-chain mutants Y58A and D97A is between 60-80% (FIG. 8). Therefore, the Kabat residues Y56, Y98, and P99 in the Z199 heavy chain contribute significantly to antigen recognition. Meanwhile, the Kabat residues Y58 and D97 in the heavy chain moderately affect the antigen-binding.

A therapeutic compound based on Z199, such as humZ199, thus preferably includes the Kabat residues Y32 in CDR1, L50 in CDR2 and P95 in CDR3 as found in the Z199 light chain, and the Kabat residues Y56 in CDR2 and both Y98 and P99 in CDR3, in the positioning found in the Z199 heavy chain.

In one aspect, the present invention provides for humanized versions of an anti-NKG2A antibody produced by the Z199 hybridoma, as well as for humanized versions of non-human antibodies sharing biological characteristics and/or substantial sequence identity with Z199. In another embodiment, the monoclonal antibody or a fragment or derivative thereof is capable of binding to a non-human primate NKG2A.

The humanized antibody herein comprises non-human hypervariable region or CDR residues incorporated into human VH and VL domains.

In one aspect, the invention provides a humanized antibody comprising antigen-binding residues from the CDRs of murine antibody Z199 in a human acceptor framework, wherein at least the 6 C-terminal amino acid residues of the CDR-H2 are the same as those in the human acceptor sequence. Such humanized antibodies can be more effective than the original murine Z199 antibody or a chimeric version thereof in, e.g., potentiating the cytotoxic activity of a CD94/NKG2A-expressing cytotoxic lymphocyte, such as, e.g., an NK-cell, an NKT-cell, an α/β T-cell, and/or a γ/δ T-cell, or of a population of CD94/NKG2A-expressing cytotoxic lymphocytes.

As shown in FIG. 4, the potential back mutations in the humZ199 VL and VH are provided in bold and underlined as human. Preferred embodiments of the invention thus entail the following back-mutated humZ199 light and heavy chain variants, using Kabat numbering:

humZ199 VL: E1Q, L46P, L47W, I58V, D70S and any combination of (E1Q, L46P, L47W, I58V, D70S)

humZ199 VH: S49A, S77T, A93T, A60P, S62T, K64T and any combination of (S49A, S77T, A93T, A60P, S62T, K64T).

Also preferred are antibodies comprising any combination of the above-indicated back-mutated humanized heavy and light chains.

In another aspect, the invention provides humanized antibodies that comprise a VH domain having at least about 50%, at least about 70%, at least about 80% sequence identity (e.g., at least about 85%, 90%, 95%, 97%, or more identity) to the VH domain of Z199 or humZ199 (cf. e.g. the sequences in FIG. 4). In another particular aspect, the invention provides a humanized antibody that binds NKG2A, comprising a VH domain that comprises non-human CDR residues incorporated into a human VH domain, wherein the VH domain is at least about 50% (such as at least 90%) identical to humZ199VH.

Various forms of the humanized antibody are contemplated. For example, the humanized antibody may be an antibody fragment, such as a Fab or other type of fragment described herein. Alternatively, the humanized antibody may be a full-length or intact antibody, such as a full-length or intact IgG1 or IgG4 antibody. In one embodiment, the humanized antibody is a full-length IgG4 antibody or a fragment thereof.

In one aspect, the present invention provides a humanized antibody characterized by: a) specifically binding to NKG2A; b) not specifically binding to an Fc receptor; and c) when bound to NKG2A on a human NK cell, causing said NK cell to lyse a target human cell bearing HLA-E on the target cell surface, when said target cell comes into contact with said NK cell. In one embodiment, the humanized antibody comprises a human IgG1 constant region (e.g. IgG1, -2 or -3) that has been modified to prevent binding to an Fc receptor, or a human IgG4 constant region. Such antibodies, as well as antibody fragments that do not bind an Fc receptor, are particularly useful in applications where it is desired to activate NK cells (e.g. cancer, infectious disease), without leading to the depletion of the NK cell themselves, as might be mediated by antibody dependent cell cytotoxicity, and can be referred to as "non-depleting" antibodies.

In another aspect, the humanized antibody comprises a human IgG1 constant region that binds an Fc receptor (e.g. IgG1, -2 or -3), or a human IgG1, 2, 3 or 4 constant region has been modified to bind an Fc receptor or increase binding to an Fc receptor, or a human $IgG_4$ constant region. In another embodiment, the monoclonal antibody or a fragment thereof is linked to a moiety that is toxic to a cell to which the antibody is bound. Such antibodies are particularly useful in applications where it is desired to deplete an NK cell, useful in certain applications such as NK-LDGL (NK-type lymphoproliferative disease of granular lymphocytes; alternatively called NK-LGL), and can be referred to as "depleting" antibodies.

For recombinant production of humanized antibodies, humanized VH and VL regions, or variant versions thereof, can be cloned into expression vectors encoding full-length or truncated constant regions from a human antibody according to standard recombinant methods (see, e.g., Sambrook et al., Molecular Cloning: A Laboratory Manual, $2^{nd}$ Ed., Cold Spring Harbor Laboratory, Cold Spring Harbor, N.Y., 1989). The result is a transfected cell line that expresses and secretes the humanized antibody molecule of interest, comprising the selected VH and VL regions and constant regions. cDNA sequences encoding the constant regions of human antibodies are known. Exemplary cDNA sequences available via, e.g., GenBank, each of which incorporated by reference in its entirety, are as follows:

Human IgG1 constant heavy chain region: GenBank accession No.: J00228;

Human IgG2 constant heavy chain region: GenBank accession No.: J00230;

Human IgG3 constant heavy chain region: GenBank accession No.: X04646;

Human IgG4 constant heavy chain region: GenBank accession No.: K01316; and

Human kappa light chain constant region: GenBank accession No.: J00241.

If desired, the class of a humanized antibody may also be "switched" by known methods. For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses.

The constant region may further be modified according to known methods. For example, in an IgG4 constant region, residue S241 may be mutated to a proline (P) residue to allow complete disulphide bridge formation at the hinge (see, e.g., Angal et al., Mol Immunol. 1993; 30:105-8).

Antibody Fragments

The humanized antibodies of the invention may be prepared as antibody fragments, or antibody fragments may be prepared from humanized full-length antibodies.

Various techniques have been developed for the production of antibody fragments of humanized antibodies. Traditionally, these fragments were derived via proteolytic digestion of full-length antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. Alternatively, Fab'-SH fragments can be directly recovered from *E. coli* and chemically coupled to form F(ab')2 fragments (Carter et al., Bio/Technology, 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv). See WO 1993/16185; U.S. Pat. No. 5,571,894; and U.S. Pat. No. 5,587,458. The antibody fragment may also be a "linear antibody", e.g., as described in U.S. Pat. No. 5,641,870, for example. Such linear antibody fragments may be monospecific or bispecific.

Bispecific antibodies are antibodies that have binding specificities for at least two different epitopes. Methods for making bispecific antibodies are known in the art, and traditional production of full-length bispecific antibodies is usually based on the coexpression of two immunoglobulin heavy-chain-light-chain pairs, where the two chains have different specificities (Millstein et al., Nature, 305: 537-539 (1983)). In the bispecific antibodies according to the present invention, at least one binding epitope is on the NKG2A protein. The anti-NKG2A-binding "arm" may be combined with an "arm" that binds to a triggering molecule on a leukocyte such as a T-cell receptor molecule (e.g. CD2 or CD3), or Fc receptors for IgG (Fcgamma-R), such as Fc-gamma-RI (CD64), Fc-gamma-RII (CD32) and Fc-gamma-RIII (CD16), so as to focus cellular defense mechanisms to the NKG2A-expressing cell. Bispecific antibodies may also be used to localize cytotoxic agents to cells that express NKG2A. These antibodies possess a NKG2A-binding arm and an arm that binds the cytotoxic agent (e.g. saporin, anti-interferon-alpha, vinca alkaloid, ricin A chain, methotrexate, or radioactive isotope hapten). Bispecific antibodies can be prepared as full-length antibodies or antibody fragments (e.g. F(ab')2 bispecific antibodies). Antibodies with more than two valencies are contemplated. For example, trispecific antibodies can be prepared. Tutt et al., J. Immunol, 147: 60 (1991).

Antibody Derivatives

Antibody derivatives within the scope of this invention include humanized antibodies conjugated or covalently bound (such as e.g. fused) to a second agent.

In one aspect of the invention, the agent is conjugated or fused to a second agent.

In a further aspect, the second agent is selected from a protracting group such as PEG, a cytotoxic agent, a detectable marker, a targeting agent.

For example, in one aspect, the invention provides immunoconjugates comprising a humanized antibody conjugated or covalently bonded to a cytotoxic agent. The term "cytotoxic agent" as used herein is a molecule that is capable of killing a cell bearing a NKG2A receptor on its cell surface. Any type of moiety with a cytotoxic or cytoinhibitory effect can be conjugated to the present antibodies to form a cytotoxic conjugate of the present invention and to inhibit or kill specific NK receptor expressing cells, including therapeutic radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

In another embodiment, the antibody is derivatized with a radioactive isotope, such as a therapeutic radionuclide or a radionuclide suitable for detection purposes. Any of a number of suitable radioactive isotopes can be used, including, but not limited to, I-131, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In other embodiments, the second agent is a detectable moiety, which can be any molecule that can be quantitatively or qualitatively observed or measured. Examples of detectable markers useful in the conjugated antibodies of this invention are radioisotopes, fluorescent dyes, or a member of a complementary binding pair, such as a member of any one of: and antigen/antibody (other than an antibody to NKG2A), lectin/carbohydrate; avidin/biotin; receptor/ligand; or molecularly imprinted polymer/print molecule systems.

The second agent may also or alternatively be a polymer, intended to increase the circulating half-life of the humanized antibody, for example. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties (e.g., a full-length antibody or antibody fragment can be conjugated to one or more PEG molecules with a molecular weight of between about 1,000 and about 40,000, such as between about 2000 and about 20,000, e.g., about 3,000-12,000).

The cytotoxic agents or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antibody Immuncon. Radiopharm. 2:217; the entire disclosures of each of which are herein incorporated by reference).

Alternatively, a fusion protein comprising the anti-NKG2A antibody and a second (cytotoxic or other) polypeptide agent may be made, e.g. by recombinant techniques or peptide synthesis.

Binding Assays

The present invention provides for antibodies that bind human NKG2A, in particular humanized versions of an anti-NKG2A antibody produced by the Z199 hybridoma.

Any of a wide variety of assays can be used to assess binding of an antibody to human NKG2A. Protocols based upon ELISAs, radioimmunoassays, Western blotting, BIA-CORE, and other competition assays, inter alia, are suitable for use and are well known in the art.

For example, simple binding assays can be used, in which a test antibody is incubated in the presence of a target protein or epitope (e.g., CD94/NKG2A or a portion thereof), unbound antibodies are washed off, and the presence of bound antibodies is assessed using, e.g., radiolabels, physical methods such as mass spectrometry, or direct or indirect fluorescent labels detected using, e.g., cytofluorometric analysis (e.g. FACScan). Such methods are well known to those of skill in the art. Any amount of binding above the amount seen with a control, non-specific antibody indicates that the antibody binds specifically to the target.

In such assays, the ability of the test antibody to bind to the target cell or human NKG2A can be compared with the ability of a (negative) control protein, e.g. an antibody raised against a structurally unrelated antigen, or a non-Ig peptide or protein, to bind to the same target. Antibodies or fragments that bind to the target cells or NKG2A using any suitable assay with 25%, 50%, 100%, 200%, 1000%, or higher increased affinity relative to the control protein, are said to "specifically bind to" or "specifically interact with" the target, and are preferred for use in the therapeutic methods described below. The ability of a test antibody to affect the binding of a (positive) control antibody against NKG2A, e.g. murine or humanized Z199, or derivatives thereof, may also be assessed.

The humanized anti-NKG2A antibodies may or may not bind human NKG2C, may or may not bind human NKG2E, or may or may not bind any of human NKG2C and E. In a particular embodiment, the monoclonal antibody or fragment binds to other human CD94/NKG2 receptors, specifically the activating receptors CD94/NKG2C and/or CD94/NKG2E, with a significantly lower affinity than to CD94/NKG2A. The NKG2C- and NKG2E-binding properties of the antibodies of the invention can be evaluated in similar assays as those described above, simply exchanging NKG2A for the molecule of interest.

In one aspect, the invention provides for humanized versions of non-human antibodies sharing biological characteristics and/or substantial sequence identity with Z199. One exemplary biological characteristic is the binding to the Z199 epitope, i.e., the region in the extracellular domain of NKG2A to which the Z199 antibody binds. To screen for antibodies that bind to the Z199 epitope, a routine cross-blocking assay, such as that described in Antibodies, A Laboratory Manual, Cold Spring Harbor Laboratory, Ed Harlow and David Lane (1988), can be performed.

In an exemplary cross-blocking or competition assay, Z199 (control) antibody and a test antibody are admixed (or pre-adsorbed) and applied to a sample containing NKG2A. In certain embodiments, one would pre-mix the control antibodies with varying amounts of the test antibody (e.g., 1:10 or 1:100) for a period of time prior to applying to the NKG2A-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control. In this assay, the binding of the (labeled) control antibody in the presence of a completely irrelevant antibody is the control high value. The control low value is be obtained by incubating the labeled (positive) control antibody (Z199) with unlabeled control antibody, where competition would occur and reduce binding of the labeled antibody.

In a test assay, a significant reduction in labeled antibody reactivity in the presence of a test antibody is indicative of a test antibody that recognizes the same epitope, i.e., one that "cross-reacts" with the labeled control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

Similar cross-blocking assays can also be used to evaluate whether a test (humanized) antibody affects the binding of the natural ligand for human CD94/NKG2A, HLA-E, to CD94/NKG2A, by exchanging Z199 for a suitable form of HLA-E. For example, to determine whether a humanized anti-NKG2A antibody preparation reduces or blocks CD94/

NKG2A interactions with HLA-E, the following test can be performed: A cell line expressing CD94/NKG2A, such as Ba/F3-CD94/NKG2A, NKL or NK92, is incubated for 30 min on ice, with increasing concentrations of a test anti-NKG2A antibody. The cells are then incubated with PE-labeled HLA-E tetramers for 30 minutes on ice, washed again, and HLA-E tetramer binding analyzed on a flow cytometer (FACScalibur, Beckton Dickinson), by standard methods. In the absence of test antibodies, the HLA-E tetramer binds to the cells. In the presence of an antibody preparation that blocks CD94/NKG2A-binding to HLA-E, there is a reduced binding of HLA-E tetramers to the cells, and such mAbs are designated "blocking antibodies". The present invention provides antibodies that reduces the inhibitory activity of human CD94/NKG2A receptor without blocking HLA-E. Accordingly, such lack of blocking can be similarly detected in these assays.

In some aspects of the invention, e.g., where it is not desired to kill NKG2A-expressing cells, the humanized antibodies of this invention preferably do not demonstrate substantial specific binding to Fc receptors. Such antibodies may comprise constant regions of various heavy chains that are known not to bind Fc receptors. One such example is an IgG4 constant region. IgG4 Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any other antibody type can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

Functional Assays

If an anti-NKG2A antibody reduces or blocks CD94/NKG2A interactions with HLA-E, it may increase the cytotoxicity of CD94/NKG2A-restricted lymphocytes. This can be evaluated by a typical cytotoxicity assay, examples of which are described below.

The ability of an antibody to reduce CD94/NKG2A-mediated signaling can be tested in a standard 4-hour in vitro cytotoxicity assay using, e.g., NKL cells that express CD94/NKG2A, and target cells that express HLA-E. Such NKL cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). The target cells are labeled with $^{51}$Cr prior to addition of NKL cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NKL effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NKL effector cells kill less efficiently HLA-E$^+$ LCL 721.221-Cw3 cells due to HLA-E-induced inhibitory signaling via CD94/NKG2A. When NKL cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion.

The inhibitory activity (i.e. cytotoxicity enhancing potential) of an antibody of this invention can also be assessed in any of a number of other ways, e.g., by its effect on intracellular free calcium as described, e.g., in Sivori et al., J. Exp. Med. 1997; 186:1129-1136, the disclosure of which is herein incorporated by reference. NK, T, or NKT cell activity can also be assessed using a cell based cytotoxicity assays, e.g., measuring chromium release or other parameter to assess the ability of the antibody to stimulate NK cells to kill target cells such as P815, K562 cells, or appropriate tumor cells as disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference.

In one embodiment, an antibody preparation causes at least a 10% augmentation in the cytotoxicity of a CD94/NKG2A-restricted lymphocyte, preferably at least a 40% or 50% augmentation in NK cytotoxicity, or more preferably at least a 70% augmentation in NK cytotoxicity.

The activity of a cytotoxic lymphocyte can also be addressed using a cytokine-release assay, wherein NK cells are incubated with the antibody to stimulate the cytokine production of the NK cells (for example IFN-y and TNF-α production). In an exemplary protocol, IFN-y production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-y or PE-IgG1 (Pharmingen). GM-CSF and IFN-y production from polyclonal activated NK cells are measured in supernatants using ELISA (GM-CSF: DuoSet Elisa, R&D Systems, Minneapolis, Minn., IFN-: OptEIA set, Pharmingen).

In a particular aspect, the invention provides antibodies that are more capable of, or more effective in, increasing the cytotoxicity of CD94/NKG2A-restricted lymphocytes, potentiating cytotoxic activity of a CD94/NKG2A-restricted lymphocyte, or reducing or inhibiting CD94/NKG2A-mediated signaling, than the original, non-humanized antibody and/or a chimeric version thereof. Such antibodies can be, for example, at least 2%, at least 5%, at least 10%, at least 15%, or at least 20% more capable or effective an original, non-humanized antibody or chimeric version thereof.

Antibody Production

The invention also provides isolated nucleic acids encoding the anti-NKG2A antibodies described herein, as well as vectors and host cells comprising such nucleic acids.

In one aspect, a nucleic acid fragment encoding the agent according to the invention is provided.

In one aspect, a nucleic acid fragment encoding the agent according to the invention, which is selected from a DNA and an RNA fragment, is provided.

Also provided for are methods of producing such anti-NKG2A antibodies using recombinant techniques such as, e.g., culturing suitable host cells comprising such nucleic acids or vectors so that the nucleic acid is expressed and the humanized antibody produced. Before culturing, the host cell may, for example, be co-transfected with a vector comprising nucleic acids encoding a variable heavy domain and with a vector comprising nucleic acid encoding a variable light domain. Additionally, the antibody may be recovered and/or purified from the host cell culture using known techniques. Useful vectors, host cells, and techniques are further described below.

Generally, for recombinant production of the antibody, a nucleic acid encoding it is isolated and inserted into a replicable vector for further cloning (amplification of the DNA) or for expression, typically operably linked to one or more expression control elements. DNA encoding the monoclonal antibody is readily isolated and sequenced using conventional procedures (e.g., by using oligonucleotide probes that are capable of binding specifically to genes encoding the heavy and light chains of the antibody). Many vectors are known and available. The vector components generally include, but are not limited to, one or more of the following: a signal sequence, an origin of replication, one or more marker genes, an enhancer element, a promoter, and a transcription-termination sequence.

Signal Sequence Component

The anti-NKG2A antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

For prokaryotic host cells that do not recognize and process the native anti-NKG2A antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, alpha-factor leader (including *Saccharomyces* and *Kluyveromyces* alpha-factor leaders), acid-phosphatase leader, the *C. albicans* glucoamylase leader, or the signal described in WO 1990/13646. In mammalian cell expression, mammalian signal sequences as well as viral secretory leaders, for example, the herpes simplex gD signal, are available.

The DNA for such precursor region is ligated in reading frame to DNA encoding the anti-NKG2A antibody.

Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, EBV, or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-NKG2A antibody-encoding nucleic acid, such as DHFR, thymidine kinase, metallothionein-I and -II, preferably primate metallothionein genes, aderosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-NKG2A antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6-μm circular plasmid pKD1 can be used for transformation of *Kluyveromyces* yeasts. Alternatively, an expression system for large-scale production of recombinant calf chymosin was reported for *K. lactis* (Van den Berg, Bio/Technology, 8:135 (1990). Stable multi-copy expression vectors for secretion of mature recombinant human serum albumin by industrial strains of *Kluyveromyces* have also been disclosed. Fleer et al., *Bio/Technolog.* 9: 968-975 (1991).

Promoter Component

Expression and cloning vectors usually contain a promoter that is recognized by the host organism and is operably linked to the anti-NKG2A antibody-encoding nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-NKG2A antibody.

Various promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP73657. Yeast enhancers also are advantageously used with yeast promoters.

Anti-NKG2A antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus (CMV), a retrovirus, hepatitis-B virus and most preferably Simian Virus 40 (SV40), heterologous mammalian promoters, e.g., the actin promoter or an immunoglobulin promoter, and heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature, 297:598-601 (1982) on expression of human β-interferon cDNA in mouse cells under the control of a thymidine kinase promoter from herpes simplex virus. Alternatively, the rous sarcoma virus long-terminal repeat can be used as the promoter.

Enhancer Element Component

Transcription of a DNA encoding the anti-NKG2A antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early-promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the anti-NKG2A antibody-encoding sequence, but is preferably located at a site 5' from the promoter.

Transcription Termination Component

Expression vectors used in eukaryotic host cells (for example, yeast, fungi, insect, plant, animal, human, or nucleated cells from other multicellular organisms) will also contain sequences necessary for the termination of transcription and for stabilizing the mRNA. Such sequences are commonly available from the 5' end, occasionally 3' end, of untranslated regions of eukaryotic or viral DNAs or cDNAs. These regions contain nucleotide segments transcribed as polyadenylated fragments in the untranslated portion of the mRNA encoding anti-NKG2A antibody. One useful transcription termination component is the bovine growth hormone polyadenylation region. See WO 1994/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g. *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-NKG2A antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-NKG2A antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney (HEK) line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub et al., Proc. Natl. Acad.

Sci. USA, 77:4216 (1980), including DG44 (Urlaub et al., Som. Cell and Mol. Gen., 12: 555-566 (1986)) and DP12 cell lines); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2).

Host cells are transformed with the above-described expression or cloning vectors for anti-NKG2A antibody production and cultured in conventional nutrient media modified as appropriate for inducing promoters, selecting transformants, or amplifying the genes encoding the desired sequences.

Culturing the Host Cells

The host cells used to produce the anti-NKG2A antibody of this invention may be cultured in a variety of media. Commercially available media such as Ham's F10 (Sigma), Minimal Essential Medium ((MEM), (Sigma), RPMI-1640 (Sigma), FreeStyle™ (Cibco) and Dulbecco's Modified Eagle's Medium ((DMEM), Sigma) are suitable for culturing the host cells. In addition, any of the media described, for example, in Ham et al., Meth. Enz. 58:44 (1979); Barnes et al., Anal. Biochem., 102:255 (1980); U.S. Pat. Nos. 4,767, 704; 4,657,866; 4,927,762; 4,560,655; or 5,122,469; WO 1990/03430; WO 1987/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Antibody Purification

When using recombinant techniques, the antibody can be produced intracellularly or in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology, 10: 163-167 (1992) describes a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulphonyl fluoride (PMSF) may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human gamma1, gamma, or gamma4 heavy chains (Lindmark et al., J. Immunol. Meth., 62:1-13 (1983)). Protein G is recommended for all mouse isotypes and for human y3 (Guss et al., EMBO J., 5:15671575 (1986)). The matrix to which the affinity ligand is attached is most often agarose, but other matrices are available. Mechanically stable matrices such as controlled-pore glass or poly(styrenedivinyl)benzene allow for faster flow rates and shorter processing times than can be achieved with agarose. Where the antibody comprises a CH3 domain, the BAKERBOND ABX™ resin (J. T. Baker, Phillipsburg, N.J.) is useful for purification. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation are also available depending on the antibody to be recovered.

Pharmaceutical Formulations

In one aspect, an agent according to the invention for use as a pharmaceutical, is provided.

In one aspect, an agent according to the invention for use as a pharmaceutical in the treatment of malignant neoplasms, viral infections, an inflammatory disorder, and an autoimmune disease, is provided.

In one aspect, an agent according to the invention for use as a pharmaceutical for neutralising or reducing the inhibitory activity of a CD94/NKG2A receptor expressed on the surface of a cell in a human patient, is provided.

In one aspect, an agent according to the invention for use as a pharmaceutical for potentiating the cell-killing activity of a CD94/NKG2A expression cell in a human patient, is provided.

In one aspect, an agent according to the invention for use as a pharmaceutical in inducing killing of a Cw3 expressing target cell in a human patient, is provided.

In a further aspect, a composition comprising an agent according to the invention together with a pharmaceutically acceptable carrier, diluent or vehicle, is provided.

In one embodiment, the present invention provides pharmaceutical composition comprising antibodies as described herein together with one or more carriers.

Accordingly, one object of the invention is to provide a pharmaceutical formulation comprising such an antibody which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. The preservative may be selected from, e.g., the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. The preservative may, e.g., be present in a concentration from 0.1 mg/ml to 20 mg/ml, from 0.1 mg/ml to 5 mg/ml, from 5 mg/ml to 10 mg/ml, or from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment, the formulation further comprises an isotonic agent. The isotonic agent may be, e.g., selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. The sugar or sugar alcohol concentration can, e.g., be between about 1 mg/ml and about 150 mg/ml. The isotonic agent can be present in a concentration from, e.g., 1 mg/ml to 50 mg/ml, from 1 mg/ml to 7 mg/ml, from 8 mg/ml to 24 mg/ml, or from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment, the formulation also comprises a chelating agent. The chelating agent can, for example, be selected from salts of ethylenediaminetetraacetic acid (EDTA), citric acid, and aspartic acid, and mixtures thereof. The chelating agent may, for example, be present in a concentration from 0.1 mg/ml to 5 mg/ml, from 0.1 mg/ml to 2 mg/ml, or from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995. More particularly, compositions of the invention can be stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment, the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment, the formulation further comprises a surfactant. The surfactant may, for example, be selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium taurodihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propane-sulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19<sup>th</sup> edition, 1995.

In a further embodiment, the formulation further comprises protease inhibitors such as EDTA (ethylenediamine tetraacetic acid) and benzamidine HCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the antibody, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of an antibody, using, for example a metered dose inhaler, dry powder inhaler and a nebulizer, all being devices well known to those skilled in the art.

Compositions of the current invention are also useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the antibody compound in the form of a nasal or pulmonal spray. As a still further option, the pharmaceutical compositions containing an antibody of the invention can also be adapted to transdermal administration, e.g. by needle-free injection or from a patch, optionally an iontophoretic patch, or transmucosal, e.g. buccal, administration.

The antibody can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardized testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

$$d_a = \sqrt{\frac{\rho}{\rho_a}} d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the antibody may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the antibody is stable for more than 6 weeks of usage and for more than 3 years of storage.

In another embodiment of the invention the pharmaceutical formulation comprising the antibody is stable for more than 4 weeks of usage and for more than 3 years of storage.

In a further embodiment of the invention the pharmaceutical formulation comprising the antibody is stable for more than 4 weeks of usage and for more than two years of storage.

In an even further embodiment of the invention the pharmaceutical formulation comprising the antibody is stable for more than 2 weeks of usage and for more than two years of storage.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Therapeutic Applications

Methods of treating a patient using an anti-NKG2A antibody as described herein are also provided for. In one embodiment, the invention provides for the use of an antibody as described herein in the preparation of a pharmaceutical composition for administration to a human patient. Typically, the patient suffers from, or is at risk for, cancer, a viral disease, an inflammatory disorder, or an autoimmune disorder. Alternatively, the antibody of the invention is used to improve bone marrow transplantation in a patient.

For example, in one aspect, the invention provides a method of potentiating the activity of CD94/NKG2A-restricted lymphocytes in a patient in need thereof, comprising the step of administering a human or humanized anti-NKG2A antibody to said patient, which antibody reduces or prevents HLA-E-mediated activation of the CD94/NKG2A receptor. In one embodiment, the method directed at increasing the activity of such lymphocytes in patients having a disease in which increased NK, T, and/or NKT cell activity is beneficial, which involves, affects or is caused by cells susceptible to lysis by NK, T, or NKT cells, or which is caused or characterized by insufficient NK, T, or NKT cell activity, such as a cancer, an infectious disease or an immune disorder.

More specifically, the methods and compositions of the present invention are utilized for the treatment of a variety of cancers and other proliferative diseases including, but not limited to: carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma, and multiple myeloma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyoscarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

Particular disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); adult T-cell leukemia lymphoma (ATLL); T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; lym-phoma/leukaemia (T-Lbly/T-ALL), multiple myeloma.

Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

In a particular aspect, antibodies of the invention are used to treat NK-type lymphoproliferative disease of granular lymphocytes; alternatively called NK-LGL), referring to a class of proliferative disorders that is caused by the clonal expansion of NK cells or NK-like cells, i.e., large granular lymphocytes showing a characteristic combination of surface antigen expression (e.g., CD3−, CD56+, CD16+, etc.; see, e.g., Loughran (1993) Blood 82:1). The cell proliferation underlying these disorders can have variable effects, ranging from the mild symptoms seen in some patients to the aggressive, often-fatal form of the disease called NK-LDGL leukemia. Symptoms of this class of disorders can include fever, mild neutropenia, thrombocytopenia, anemia, lymphocytosis, splenomegaly, hepatomegaly, lymphadenopathy, marrow infiltration, and others (see, e.g., Zambello et al. (2003) Blood 102:1797; Loughran (1993) Blood 82:1; Epling-Burnette et al. (2004) Blood-2003-02-400).

The CD94/NKG2A antibody based treatment can also be used to treat or prevent infectious diseases, including preferably any infections caused by infection by viruses, bacteria, protozoa, molds or fungi. Such viral infectious organisms include, but are not limited to, hepatitis type A, hepatitis type B, hepatitis type C. influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2). Bacteria constitute another preferred class of infectious organisms including but are not limited to the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponerna; Camplyobacter, Pseudomonas* including *P. aeruginosa; Legionella; Neisseria* including *N. gonorrhoeae* and *N. meningitides; Flavobacterium* including *F. meningosepticum* and *F. odoraturn F. odoratum; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. fickettsfi, Chlamydia* including *C. psittaci* and *C. trachomatis; Mycobacterium* including *M. tuberculosis, M. intracellulare, M. fortuitum, M. laprae, M. avium, M. bovis, M. africanum,*

*M. kansasii, M. intracellulare,* and *M. lepraernurium*; and *Nocardia.* Protozoa may include but are not limited to, *leishmania, kokzidioa,* and *trypanosoma.* Parasites include but are not limited to, *chlamydia* and *rickettsia.* A complete list of infectious diseases can be found on the website of the National Center for Infectious Disease (NCID) at the Center for Disease Control (CDC) (World-Wide Web (www) address cdc.gov/ncidod/diseases/), which list is incorporated herein by reference. All of these diseases are candidates for treatment using the inhibitory anti-CD94/NKG2A antibodies of the invention.

In an alternative aspect, the anti-NKG2A antibodies are used to target and kill NKG2A-expressing cells in, e.g., a patient suffering from a cancer characterized by CD94/NKG2A expression on cancerous cells, for example an NK- or T-cell lymphoma. In one embodiment, the humanized antibody is administered in the form of an immunoconjugate comprising the humanized antibody and a cytotoxic agent.

In alternative aspect, the anti-NKG2A antibodies are used to treat or prevent an autoimmune or inflammatory disorder. Exemplary autoimmune disorders treatable using the present methods include, inter alia, hemolytic anemia, pernicious anemia, polyarteritis nodosa, systemic lupus erythematosus, Wegener's granulomatosis, autoimmune hepatitis, Behcet's disease, Crohn's disease, primary bilary cirrhosis, scleroderma, ulcerative colitis, Sjogren's syndrome, Type 1 diabetes mellitus, uveitis, Graves' disease, Alzheimer's disease, thyroiditis, myocarditis, rheumatic fever, scleroderma, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, Bullous pemphigoid, Hashimoto's thyroiditis, psoriasis, and vitiligo.

Examples of inflammatory disorders that can be treated by these methods include, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, selerochoroiditis, scrotitis, sinusitis, spondylitis, steatitis, stomatitis, synovitis, syringitis, tendonitis, tonsillitis, urethritis, and vaginitis.

It has also been shown that alloreactive NK cell killing of dendritic cells improved engraftment of hematopoietic cells in a bone marrow transplant (L. Ruggeri et al., Science, 2002, 295:2097-2 100). Thus, in another embodiment, the invention provides a method of improving the engraftment of hematopoietic cells in a patient comprising the step administering to said patient a composition of this invention comprising an activating antibody. Improvement in grafting is manifest by any one of reduced incidence or severity of graft versus host disease, prolonged survival of the graft, or a reduction in or elimination of the symptoms of the disease being treated by the graft (e.g., a hematopoietic cancer). This method is preferably used in the treatment of leukemia.

Combination Treatments

A number of therapeutic agents are available for the treatment of cancers. The antibody compositions and methods of the present invention may thus also be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the anti-CD94/NKG2A antibody-based treatment, its combination with the present invention is contemplated.

In connection with solid tumor treatment, the present invention may be used in combination with classical approaches, such as surgery, radiotherapy, chemotherapy, and the like. The invention therefore provides combined therapies in which anti-CD94/NKG2A antibodies according to the invention are used simultaneously with, before, or after surgery or radiation treatment; or are administered to patients with, before, or after administration of another anti-cancer agent. One would ensure that the surgery, radiotherapy, or anti-cancer agent in combination with the active agent in the composition of this invention exert an advantageously combined effect on the cancer.

Exemplary anti-cancer agents include chemotherapeutic agents, hormonal agents, anti-angiogenic agents, anti-metastatic agents, anti-cancer antibodies (e.g., Rituximab), antibodies against inhibitory KIR-molecules, growth-factor inhibitors, apoptosis-promoting compounds, cytokines and other immunomodulatory agents, tumor-targeting agents conjugated to toxins or radionuclides, compounds that interfere with DNA replication, mitosis and chromosomal segregation, and agents that disrupt the synthesis and fidelity of polynucleotide precursors.

For autoimmune or inflammatory disorders, any other compound known to be effective for one or more types of autoimmune or inflammatory disorders, or any symptom or feature of autoimmune or inflammatory disorders, including inter alia, immunosuppressants, e.g., azathioprine (e.g., Imuran), chiorambucil (e.g., Leukeran), cyclophosphamide (e.g., Cytoxan), cyclosporine (e.g., Sandimmune, Neoral), methotrexate (e.g., Rheumatrex), corticosteroids, prednisone (e.g., Deltasone, Meticorten), Etanercept (e.g., Enbrel), infliximab (e.g., Remicade), inhibitors of TNF, FK-506, raparnycin, mycophenolate mofetil, leflunomide, anti-lymphocyte globulin, deoxyspergualin or OKT.

Preferred examples of immunomodulatory compounds include cytokines. Other examples include compounds that have an effect, preferably an effect of activation or potentiation NK cell activity, or of inducing or supporting the proliferation of NK cells. Other compounds for administration before, simultaneously with, or after compositions comprising the agents of the invention are adjunct compounds (e.g., anti-emetics and analgesic agents) and anti-viral agents.

As will be understood by those of ordinary skill in the art, the appropriate doses of anti-cancer agents will approximate those already employed in clinical therapies wherein the anti-cancer agents are administered alone or in combination with other agents. Variation in dosage will likely occur depending on the condition being treated. The physician administering treatment will be able to determine the appropriate dose for the individual subject.

Articles of Manufacture

In another embodiment of the invention, an article of manufacture containing materials useful for the treatment of the disorders described above is provided. For example, the article of manufacture can comprise a container containing an antibody as described herein together with instructions directing a user to treat a disorder such as a cancer or a viral disease in a mammal with the antibody in an effective amount. In a preferred embodiment, the mammal is a human. The article of manufacture typically comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the humanized anti-NKG2A antibody herein, or an antibody derivative (e.g., an immunoconjugate) comprising such a humanized antibody. The label or package insert indicates that the composition is used for treating the condition of choice, such as cancer or a viral disease.

Moreover, the article of manufacture may comprise (a) a first container with a composition contained therein, wherein the composition comprises the antibody described herein, and (b) a second container with a composition contained therein, wherein the composition comprises a therapeutic agent other than the first antibody. The article of manufacture in this embodiment of the invention may further comprise a package insert indicating that the first and second compositions can be used in combination to treat a cancer or viral disease. Such therapeutic agent may be any of the adjunct therapies described in the preceding section (e.g., a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Administration

As described above, several monoclonal antibodies have been shown to be efficient in clinical situations (such as, e.g., Rituxan (Rituximab) and others), and similar administration regimens (i.e., doses and/or administration protocols) may be used with the antibodies of this invention. Schedules and dosages for administration can be determined in accordance with known methods for these products, for example using the manufacturers' instructions. For example, an antibody preparation can be supplied at a concentration of 10 mg/mL in either 100 mg (10 mL) or 500 mg (50 mL) single-use vials. An exemplary suitable dosage range for an antibody of the invention may between about 10 mg/m$^2$ and 500 mg/m$^2$. Quantities and schedule of injection of anti-NKG2A antibodies that, e.g., saturate cells for 24 hours, 48 hours 72 hours or a week or a month can be determined considering the affinity of the antibody and its pharmacokinetic parameters. However, it will be appreciated that these schedules are exemplary and that optimal schedule and regimen and the tolerability of the antibodies must be determined in clinical trials.

Non-Therapeutic Applications

The antibodies (e.g. the humanized anti-NKG2A antibodies) of the invention also have non-therapeutic applications.

For example, the antibodies may be used as affinity-purification agents. In this process, the antibodies are immobilized on a solid phase such as a SEPHADEX™ resin or filter paper, using methods well known in the art. The immobilized antibody is contacted with a sample containing the NKG2A protein (or fragment thereof) to be purified, and thereafter the support is washed with a suitable solvent that will remove substantially all the material in the sample except the NKG2A protein, which is bound to the immobilized antibody. Finally, the support is washed with another suitable solvent, such as glycine buffer, pH 5.0, that will release the NKG2A protein from the antibody.

Anti-NKG2A antibodies may also be useful in diagnostic assays for NKG2A protein, e.g. detecting its expression in specific cells, tissues, or serum.

For diagnostic applications, the antibody typically will be labeled with a detectable moiety. Numerous labels are available that can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, "Methods for the Preparation of Enzyme-Antibody Conjugates for use in Enzyme Immunoassay," in Methods in Enzym. (Ed., J. Langone & H. Van Vunakis), Academic Press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) beta-D-galactosidase (beta-D-Gal) with a chromogenic substrate (e.g., p-nitrophenyl-beta-D-galactosidase) or fluorogenic substrate 4-methylumbelliferyl-p-beta-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin, and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-NKG2A antibody need not be labeled, and the presence thereof can be detected using a labeled secondary antibody that binds to the NKG2A antibody.

The antibodies of the present invention may be employed in any known assay method, such as competitive-binding assays, direct and indirect sandwich assays, and immunoprecipitation assays. Zola, Monoclonal Antibodies: A Manual of Techniques, pp. 147-158 (CRC Press, Inc. 1987).

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide or a non-radioactive indicator detectable by, e.g., nuclear magnetic resonance, or other means known in the art. Preferably, the label is a radiolabel, such as, e.g., $^{125}$I, $^{131}$I, $^{67}$Cu, $^{99m}$Tc, or $^{111}$In. The labeled antibody is administered to a host, preferably via the bloodstream, and the presence and location of the labeled antibody in the host is assayed. This imaging technique is suitably used in the detection, staging and treatment of neoplasms. The radioisotope is conjugated to the protein by any means, including metal-chelating compounds or lactoperoxidase, or iodogen techniques for iodination.

As a matter of convenience, the antibodies of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

EXAMPLES

Further details of the invention are illustrated by the following non-limiting Examples.

Example 1

Z199 is a Non-Competitive CD94/NKG2A Antagonist

This Example describes the evaluation of the antagonistic and HLA-E-blocking capability of HP-3D9, Z270, and Z199.
Materials & Methods
Z199 Induces the Killing of HLA-E Expressing Tumor-Cells by CD94/NKG2A-Restricted NK-Cells. HLA-E is the functional ligand for the NK-inhibitory receptor CD94/NKG2A, as shown in FIG. 1. This figure contains a representative $^{51}$Cr-release cytotoxicity assay, in which the capacity of CD94/NKG2A$^+$ NKL cells to kill $^{51}$Cr-labeled LCL 721.221 (functionally HLA-E$^-$) or LCL 721.221-Cw3 cells (functionally HLA-E$^+$) is depicted. In these assays, effector cells (E) are incubated with $^{51}$Cr-labeled target-cells (T), at various E:T ratio's, in a humidified incubator containing 5% CO$_2$, for 4 hours at 37° C. The killing of target-cells is analyzed by measuring the amount of $^{51}$Cr in the tissue-culture medium, which is released by target cells upon killing. The killing is annotated as a percentage of the maximal possible killing (i.e. when all cells are lysed), corrected for the spontaneous release of $^{51}$Cr by cells in the same period. In a formula specific killing (%) is defined as:

$$\frac{100 * (^{51}\text{Cr-release in sample} - \text{spontaneous }^{51}\text{Cr-release})}{(\text{maximal }^{51}\text{Cr-release} - \text{spontaneous }^{51}\text{Cr-release})}$$

In FIG. 1, it is apparent that NKL cells kill less efficiently tumour-cells that express functional HLA-E (triangles) in comparison with tumour-cells that lack functional HLA-E (diamonds). When NKL cells were pre-incubated with saturating concentrations of the mouse mAb's HP-3D9 (anti-CD94) or Z199 (anti-NKG2A), HLA-E$^+$ target-cells were much more efficiently killed (crosses), at levels comparable to that of HLA-E$^-$ tumour-cells in the same assay. Thus, HLA-E restricts the killing of target-cells by CD94/NKG2A-expressing effector cells (e.g. NK, NKT, α/βαT-cells and γ/δ T-cells), which can be prevented by mAb's that functionally block CD94/NKG2A.

Z199 is a Non-Competitive CD94/NKG2A Antagonist.
To test whether CD94/NKG2A-inhibitory antibodies prevent ligand (i.e. HLA-E) binding to CD94/NKG2A, we analyzed whether HP-3D9 and Z199 could prevent the binding of HLA-E tetramers to CD94/NKG2A over-expressing Ba/F3 cells (Ba/F3-CD94/NKG2A). For this, Ba/F3-CD94/NKG2A was incubated with 1) mAb's (HP-3D9 (10 µg/ml) or Z199 (10 µg/ml)), 2) with PE-labeled HLA-E tetramers (4.7 µg/ml), or 3) first incubated with mAb's and then incubated with PE-labeled HLA-E tetramers. All incubations were performed in tissue-culture medium containing 2% FCS, on ice. Subsequently, after washing, cells were incubated with APC-conjugated secondary antibodies specific for mouse Ab's, and analyzed by flowcytometry using a BD Biosciences FACSarray. As shown in FIG. 2, HP-3D9 (2A) and Z199 (2D) cause a shift of the cell population along the Y-axis, out of the gate were unstained cells reside (lower left quadrant). In contrast, HLA-E (2B, 2E) causes a shift of the cell population along the X-axis, out of the lower left quadrant where unstained cells reside. Both antibodies and HLA-E tetramers could not bind Ba/F3-NKG2D cells, indicating that they specifically bind CD94/NKG2A on Ba/F3-CD94/NKG2A cells in these assays. When Ba/F3-CD94/NKG2A cells were first incubated with HP-3D9, and subsequently with HLA-E tetramers, binding of HLA-E tetramers could not be detected (FIG. 2C). HP-3D9 thus prevents HLA-E binding to CD94/NKG2A, and the CD94/NKG2A-inhibitory effect of this mAb in NK-cytotoxicity assays (FIG. 1) is therefore a consequence of preventing that HLA-E can induce negative signals to cytotoxic lymphocytes via CD94/NKG2A. As such, HP-3D9 can be considered a competitive CD94/NKG2A antagonist. In contrast, when Ba/F3-CD94/NKG2A cells were first incubated with Z199, and subsequently with HLA-E tetramers, binding of both Z199 and HLA-E tetramers to the cells could be detected, as shown by the double-positive cells in right upper quadrant in FIG. 2F. Since Z199 does not prevent HLA-E binding to CD94/NKG2A, the CD94/NKG2A-inhibitory effect of Z199 in NK-cytotoxicity assays, such as shown in FIG. 1, is likely not the effect of preventing that HLA-E can induce negative signals to cytotoxic lymphocytes via CD94/NKG2A. As such, Z199 can be considered a non-competitive CD94/NKG2A antagonist.

The observations shown in FIG. 2 were confirmed in Bia-Core experiments. In these experiments, scCD94/NKG2A-mFc, an Fc-fusion protein consisting of murine IgG1 fused at the C-terminus with a single-chain construct consisting of the extracellular parts of CD94 and NKG2A, was immobilized on the chip and subsequently saturated with HP-3D9 or Z199. Subsequently, the binding of HLA-E tetramers to the protein-complexes was analyzed. Whereas HP-3D9 saturated scCD94/NKG2A could not bind HLA-E tetramers, HLA-E tetramers could bind scCD94/NKG2A saturated with Z199 (FIG. 3). These results confirm that Z199 does not prevent HLA-E binding to CD94/NKG2A, and that its ability to functionally block CD94/NKG2A is based on non-competitive antagonism.

Results

All of HP-3D9 (anti-CD94) (FIG. 1A), Z199 (anti-NKG2A) (FIG. 1B) and Z270 (anti-NKG2A) efficiently induced killing of HLA-E expressing target cells by CD94/NKG2A-restricted lymphocytes. As shown in FIGS. 2A and 2B, HP-3D9 prevented the interaction between CD94/NKG2A and its ligand, HLA-E, while Z199 did not prevent this interaction. Z270 also prevented the interaction between CD94/NKG2A and HLA-E.

When cells were pre-incubated with a saturating dose of HLA-E tetramers, all doses of humZ199 tested (from 100 pg/ml up to 1 µg/ml) were able to bind Ba/F3-CD94/NKG2A cells, although the KD of binding was somewhat affected (~1 log), which is likely due to some steric hindrance caused by the tetrameric nature of the HLA-E complexes used (data not shown).

Z199 and humZ199 are therefore non-competitive CD94/NKG2A antagonists. While not limited to theory, it is possible that Z199 interferes with CD94/NKG2A signalling by, e.g., preventing or inducing conformational changes in the CD94/NKG2A receptor, and/or affecting dimerization and/or clustering of the CD94/NKG2A receptor.

Example 2

Humanization of Z199 cDNA's encoding the variable domains in the heavy (Z199.H) and light (Z199.L) chain of Z199 were obtained by 5' RACE- and RT-PCR cloning from mRNA extracted from the Z199 hybridoma.

Sequences of Z199 VH (1 sequence) and VL (1 sequence) were obtained by cloning (5' RACE and RT PCR, NN China) from the Z199 hybridoma.

Z199 VL:

(SEQ ID NO: 1)
caaattgttctcacccagtctccagcactcatgtctgcgtctccagggga gaaggtcaccatgacctgcagtgccagctcaagtgtaagttacatttact ggtaccagcagaagccaagatcctcccccaaaccctggatttatctcaca tccaacctggcttctggagtccctgctcgcttcagtggcagtgggtctgg gacctcttactctctcacaatcagcagcatggaggctgaagatgctgcca cttattactgccagcagtggagtggtaacccgtacacgttcggaggggggg accaagctggaaataaaacgg The translated sequence:

(SEQ ID NO: 2)
QIVLTQSPALMSASPGEKVTMTCSASSSVSYIYWYQQKPRSSPKPWIYLT

SNLASGVPARFSGSGSGTSYSLTISSMEAEDAATYYCQQWSGNPYTFGGG

TKLEIKR

Z199 VH:

(SEQ ID NO: 3)
gaagttcaactggtggagtctgggggaggcttagtgaagcctggagggtc cctgaaactctcttgtgcagcctctggattcactttcagtagctatgcca tgtcttgggttcgccagtctccagagaagaggctggagtgggtcgcagaa attagtagtggtggtagttacacctactatccagacactgtgaccggccg attcaccatctccagagacaatgccaagaacaccctgtacctggaaatca gcagtctgaggtctgaggacacggccatgtattactgtacaaggcatggt gactaccctaggttcttcgatgtctggggcgcagggaccacggtcaccgt ctcctca The translated sequence:

(SEQ ID NO: 4)
EVQLVESGGGLVKPGGSLKLSCAASGFTFSSYAMSWVRQSPEKRLEWVAE

ISSGGSYTYYPDTVTGRFTISRDNAKNTLYLEISSLRSEDTAMYYCTRHG

DYPRFFDVWGAGTTVTVSS

The affinity has been validated by expression.

From an analysis of the Z199 sequences the CDRs according to the Kabats definitions are:

| CDR_L1: | CDR_L2: | CDR_L3: |
|---|---|---|
| SASSSVSYIY | LTSNLAS | QQWSGNPYT |
| SEQ ID NO: 4 | SEQ ID NO: 4 | SEQ ID NO: 4 |
| pos. 24-33 | pos. 49-55 | pos. 88-96 |

| CDR_H1: | CDR_H2: | CDR_H3: |
|---|---|---|
| SYAMS | EISSGGSYTYYPDTVTG | HGDYPRFFDV |
| SEQ ID NO: 2 | SEQ ID NO: 2 | SEQ ID NO: 2 |
| pos. 31-35 | pos. 50-66 | pos. 99-108 |

A 3D protein structure model was build using MOE with the structural template PDB: 1MHP. Based on a statistical analysis of 201 antibody-antigen complexes in the PDB database the most probable residues in the paratope are Heavy chain: 23-35, 49-58, 93-102; Light chain: 24-34, 49-56, 89-97. Using MOE residues interacting (Hydrophobic, hydrogen binding, charge) with the paratope were identified and the combined set of residues (paratope+interacting residues) were taken as the mask of Z199.

Searching the germline V databases with the Z199.L and Z199.H returns the following potential framework templates (E-value given in parenthesis):

Heavy chain: VH3_21 (1e-044), VH3_23 (1e-043), VH3_11 (3e-043), VH3_07 (6e-043), VH3_48 (8e-043)

Light chain: VKVI_A14 (3e-033), VKIII_L6 (1e-032), VKI_L23 (2e-031), VKI_L8 (3e-031), VKI_L15 (3e-031)

Searching the germline databases with the mask returns the following potential framework templates (E-value given in parenthesis):

Heavy chain: VH3_23 (1e-012), VH3_21 (1e-012), VH3_30_3 (4e-012), VH3_64 (7e-012), VH3_30_5 (1e-011)

Light chain: VKIII_L6 (3e-007), VKI_L23 (6e-007), VKIII_A11 (1e-006), VKIII_A27 (2e-006), VKIII_L20 (3e-006)

After manual inspections of the alignments and the hits, VH3_21 and VKIII_L6 were selected as the human scaffolds, but in principle many other templates could have been chosen e. g. to optimize the physical-chemical properties of the humanized protein. JH3 and JK2 are chosen as germline J-segments.

The humanization could now be performed with the following rules:

Residues outside the mask are taken as human.
Residues inside the mask and inside the Kabat CDR are taken as murine.
Residues inside the mask and outside the Kabat CDR with mouse/germline consensus are taken as the consensus sequence.
Residues inside the mask and outside the Kabat CDR with mouse/germline difference are subject to potential back mutations.

The analysis is illustrated in FIG. 4 for Z199.L and Z199.H (mask shown by underlined sequence numbers, Kabat CDRs (using the humanized sequence as reference) shown by bold sequence numbers, mouse/germline differences in gray, potential somatic hypermutated residues shown by underlined residue letters, and potential backmutation residues shown by bold residue letters).

The resulting sequences hum Z199 VL and humZ199 VH are given with the potential back mutation residues as human. The variants of humanized Z199 are as follows:

humZ199 VL: Wild-type, E1Q, L46P, L47W, I58V, D70S and any combination of E1Q, L46P, L47W, I58V, and D70S.

humZ199 VH: Wild-type, S49A, S77T, A93T and any combination of S49A, S77T, A93T.

Humanized Z199 variants with heavy and light chains comprising different combinations of the VH and VL variants described above can also be produced and tested for properties of interest.

by transient over-expression in HEK2936E cells. In a similar fashion, humanized Z199 (humZ199) variants were produced, including those shown in FIG. 6.

All antibodies produced were harvested with Protein A-beads. To find the optimal humanized humZ199 VL and humZ199 VH combination, the capacity of Z199 variants to bind CD94/NKG2A was determined using a Biacore T-100, using an immobilized single chain (sc)CD94/NKG2A-mouse Fc fusion protein as antigen.

The antigen-binding properties of humZ199 variants were analyzed on Biacore T100 (Biacore AB, Uppsala, Sweden). Antigen sc-NKG2A-CD94-mFc was covalently immobilized on the sensor CM5 chip (Biacore AB, Uppsala, Sweden) via amine groups using 1-ethyl-3-(3-dimethylaminopropyl) carbodiimide hydrochloride (EDC) and N-hydroxysuccinimide (NHS). The immobilization level was targeted at 300 RU. For the binding analysis, purified antibody variants were diluted to 10 nM in the running buffer HBS-EP (10 mM HEPES pH 7.4, 150 mM NaCl, 3 mM EDTA, 0.005% (v/v) Tween-20). For the kinetics studies, Z199 antibody variants were diluted to a concentration series (1.25, 2.5, 5, 7.5, and 10 nM) in the HBS-EP buffer. All the samples were then injected over immobilized antigen for 2 min at the flow rate of 40 ul/min. Subsequently, the running buffer was injected for 4 min at 40 ul/min for antibody dissociation analysis. After each run, the regeneration buffer (10 mM NaOH, 500 mM NaCl) was injected (30 seconds, 10 ul/min) to completely strip the remaining antibodies off the antigen. Data were evaluated with Biacore T100 evaluation software.

Results

Initially, humanized Z199 antibody was found not able to bind to the antigen. Therefore, back mutation was introduced to the light chain and heavy chain of humZ199. Interestingly, one back mutation L46P in the light chain enabled the antibody recognize and bind to the antigen (FIG. 5). The affinity of this mutant was determined as 72 pM, which was only 2.7 fold less than KD of chimeric Z199 (24 pM) (Table 1). Other back mutations, combined with L46P in the light chain, didn't significantly further enhance the antibody affinity (FIG. 6). Therefore, humZ199 with single back mutation L46P in the light chain was selected for further characterization.

TABLE 1

| | ChimZ199 | | | | HumZ199 (LC: L46P) | | | |
|---|---|---|---|---|---|---|---|---|
| ka (1/Ms) | kd (1/s) | KD (M) | Chi$^2$ (RU$^2$) | | ka (1/Ms) | kd (1/s) | KD (M) | Chi$^2$ (RU$^2$) |
| 1.716E+6 | 4.168E−5 | 2.429E−11 | 0.731 | | 1.701E+6 | 1.224E−4 | 7.197E−11 | 0.443 |

The CDRs of the novel, humanized antibody according to the Kabat definitions are:

```
CDR_L1:         CDR_L2:         CDR_L3:
SASSSVSSYIY     LTSNLAS         QQWSGNPYT
SEQ ID NO: 5    SEQ ID NO: 6    SEQ ID NO: 7

CDR_H1:         CDR_H2:              CDR_H3:
SYAMS           EISSGGSYTYYADSVKG    HGDYPRFFDV
SEQ ID NO: 8    SEQ ID NO: 9         SEQ ID NO: 10
Note the differences compared to the murine CDRs, which are in
CDR_L1 and CDR_H2 (shown in bold).
```

Example 3

Biacore Analysis of humZ199 and Back-Mutation Variants

The murine (recZ199) and chimera (chimZ199, which consists of the constant domains of human IgG4 which have been fused to the variable domains of Z199) were produced Example 4

Identification of Critical Residues in Z199 Variable Sequence

An alanine scan was conducted to identify the critical residues in Z199 variable sequence.

Based on the in silico structure analysis of the Z199 antibody, fifteen light-chain and 9 heavy-chain ala-scan mutants were created, using chimZ199 as the basis, to determine critical residues in Z199 for binding to CD94/NKG2A and thereby exerting its antagonist function (cf. FIG. 7 for an overview of the Ala scan variants). The following is a list of mutants produced:

LC: S24A, S26A, S27A, S28A, S30A, Y32A, Y49A, L50A, S52A, N53A, L54A, S56A, S92A, N94A, P95A.

HC: T28A, S30A, S31A, Y56A, Y58A, D97A, Y98A, P99A, V102A.

The mutants were expressed individually in HEK293 cells, and tissue-culture medium containing the expressed antibodies were tested on Biacore T100 (Biacore AB, Uppsala, Sweden) for their binding profile to scCD94/NKG2A:

Antigen sc-NKG2A-CD94-mFc was covalently immobilized on the sensor CM5 chip (Biacore AB, Uppsala, Sweden) via amine groups using 1-ethyl-3-(3-dimethylaminopropyl) carbodiimide hydrochloride (EDC) and N-hydroxysuccinimide (NHS). The immobilization level was targeted at 300 RU. Purified Z199 alanine mutants were diluted to 5 nM or 10 nM in the running buffer HBS-EP. All the samples were then injected over the immobilized antigen for 4 min at the flow rate of 10 μl/min. Subsequently, the running buffer was injected for 1 min at 10 μl/min for antibody binding stability analysis. After each run, the regeneration buffer (10 mM NaOH, 500 mM NaCl) was injected (30 seconds, 10 μl/min) to completely strip the remaining antibodies off the antigen. Data were evaluated with Biacore T100 evaluation software. The relative binding of each mutant was calculated through dividing its binding level (RU) obtained from Biacore by that of chimZ199.

Results

As compared to chimZ199, all ala-scan samples showed a comparable binding profile at the two mAb concentrations used in the assay (2.5 nM and 5 nM), with the exception of Z199 variants were residues Y32, L50 or P95A were substituted for an alanine in chimZ199 VL, or residues Y56, Y98 or P99 were substituted for an alanine in chimZ199 VH.

Z199 heavy-chain alanine mutants Y56A, Y98A, and P99A retained around 40% of the antigen-binding abilities whereas the relative binding of heavy-chain mutants Y58A and D97A is between 60-80% (FIG. 8). Therefore, the amino acids Y56, Y98, and P99 in the Z199 heavy chain contribute significantly to antigen recognition. Further, the amino acids Y58 and D97 in the heavy chain moderately affect the antigen-binding.

Similarly, Z199 light-chain alanine mutants Y32A, L50A, and P95A demonstrated around 40% antigen-binding abilities. The relative binding of light-chain mutant Y49A is between 60-80% (FIG. 9). Therefore, the amino acids Y32, L50, and P95 in the Z199 light chain significantly contribute to recognize the antigen whereas the amino acid Y49 in the light chain moderately affects the antigen-binding.

A therapeutic compound based on Z199, such as humZ199, thus preferably includes the positioning of Y32 in CDR1, L50 in CDR2 and P95 in CDR3 as found in Z199_L, and the positioning of Y56 in CDR2 and both Y98 and P99 in CDR3 as found in Z199_H. These Kabat positions correspond to amino acid residues Y31, L49, and P94 of the Z199 VL domain (SEQ ID NO:2), and amino acid residues Y57, Y102, and P103 of the Z199 VL domain (SEQ ID NO:4), respectively.

Example 5

Identification of Z199 Epitope

A non-competitive anti-NKG2A antagonist antibody like Z199 can bind to CD94/NKG2A simultaneously with HLA-E. The antibody therefore binds extracellular NKG2A-residues that remain exposed when HLA-E is bound to the CD94/NKG2A complex. Further, the antibody does not break the CD94 interaction, since HLA-E binds only intact CD94/NKG2A receptor.

Using the 3D structure of the HLA-E complexed to NKG2A/CD94 (Petrie, E. J., et al. (2008), J. Exp. Med. 205: 725-735), the extracellular NKG2A residues with exposed side-chain atoms (Probe radius 4.0 Å used) were identified. Residues P94-K112 were not visible in the 3D structure and were therefore assumed to all be exposed.

As shown in FIG. 10, the epitope of a non-competitive NKG2A antibody must therefore include residues in one or more of the following segments: P94-H115, H118, P120-E122, S127-N128, Y132, K135-T139, E141-E142, L144-L145, T148-N151, S153, D158-E161, K164, F178-N190, L192-A193, K195-E197, K199-N207, N214-R215, Q220-C221, S224, H231-K232, and any combinations thereof.

The amino acid sequences of NKG2A and NKG2C are highly similar (see FIG. 11). The NKG2A epitope of antibodies that are specific for NKG2A and bind to NKG2C with a much lower affinity (such as Z199) therefore comprise exposed residues that only exist in the NKG2A sequence. Accordingly, a non-competitive antagonistic anti-NKG2A antibody binds to an epitope in the stalk or a loop corresponding, respectively, to residues P94-N107 and M189-E197 of the full-length NKG2A sequence. Preferably, the epitope of the antibody comprises at least one, at least 2, at least 3, at least 4, or at least 5 exposed residues in these segments, more specifically residues P94, S95, T96, L97, I98, Q99, R100, H101, L106, M189, E197 of the full-length NKG2A sequence (SEQ ID NO:11).

In conclusion, the NKG2A epitope of an anti-NKG2A antibody that does not compete with HLA-E. does not break the CD94 interaction, and binds with a much higher affinity to NKG2A than to NKG2C must therefore comprise residues in either or both of the following segments: PSTLIQRHNNSSLN (P94 to N107) or MNGLAFKHE (M189 to E197) of the NKG2A sequence (SEQ ID NO:11).

EXEMPLARY EMBODIMENTS

The following paragraphs describe exemplary embodiments of the invention.

1. An agent that binds to an extra-cellular portion of human CD94/NKG2A receptor, wherein the agent
   (a) reduces the inhibitory activity of human CD94/NKG2A receptor expressed on the surface of a CD94/NKG2A positive lymphocyte; and
   (b) is capable of binding CD94/NKG2A simultaneously with HLA-E, wherein the agent is not the murine 2199 antibody.
2. The agent according to embodiment 1, wherein the CD94/NKG2A positive lymphocyte is a NK cell.
3. The agent according to embodiment 1, wherein the CD94/NKG2A positive lymphocyte is a NKT cell.
4. The agent according to embodiment 1, wherein the CD94/NKG2A positive lymphocyte is a cytotoxic T cell.
5. The agent according to any one of the preceding embodiments, wherein the agent reduces CD94/NKG2A-mediated inhibition of a CD94/NKG2A-expressing lymphocyte by interfering with HLA-E induced CD94/NKG2A signalling.
6. The agent according to any one of the preceding embodiments, wherein the agent binds to an extracellular portion of CD94/NKG2A with a KD at least a 100-fold lower than to activating CD94/NKG2 molecules such as CD94/NKG2C.
7. The agent according to any one of the preceding embodiments, which competes with antibody Z199 in binding to the extra-cellular portion of human CD94/NKG2A.
8. The agent according to anyone of the preceding embodiments, which is selected from an antibody, an antibody fragment, and a synthetic or semi-synthetic antibody-derived molecule, which includes at least CDRs from an antibody which competes with the Z199 antibody for binding to CD94/NKG2A.
9. The agent according to embodiment 8, which is a fully human antibody, a humanized antibody, or a chimeric antibody.
10. The agent according to embodiment 9, which is an IgA, an IgD, an IgG, an IgE or an IgM.
11. The agent according to embodiment 10, which is an IgG1, IgG2, IgG3 or IgG4.

12. The agent according to embodiment 8, which is a fragment of an antibody according to embodiment 10 or 11.
13. The agent according to embodiment 8, wherein the antibody fragment is selected from a Fab fragment, a Fab' fragment, a Fab'-SH fragment, a F(ab)2 fragment, a F(ab')2 fragment, an Fv fragment, a Heavy chain Ig (a llama or camel Ig), a VHH fragment, a single domain FV, and a single-chain antibody fragment.
14. The agent according to embodiment 8, wherein the synthetic or semisynthetic antibody-derived molecule is selected from a scFV, a dsFV, a minibody, a diabody, a triabody, a kappa body, an IgNAR, a tandAb, a BiTE; and a multispecific antibody.
15. The agent according to any preceding embodiment, which comprises CDR sequences from the Z199 VH and VL domains.
16. The agent according to embodiment 15, which comprises one, two, three, four, five, or six back-mutations in the Z199 CDR sequences.
17. The agent according embodiment 16, which comprises amino acid residues 31-35, 50-60, 62, 64, 66, and 99-108 of the Z199 variable-heavy (VH) domain (SEQ ID NO: 4) and amino acid residues 24-33, 49-55, and 88-96 of Z199 variable-light (VL) domain (SEQ ID NO: 2).
18. The agent according to embodiment 17, which is a fully human or a humanized antibody comprising a proline at position 46 of the light chain.
19. The agent according to embodiment 10, which includes human framework regions selected from the group consisting of recombined germline sequences and associated somatic hypermutation.
20. The agent according to any one of embodiments 10-12, which is a fully human antibody which has been raised against the CD94/NKG2A epitope which binds antibody Z199 or raised against an anti-idiotypic antibody specifically binding the idiotype of Z199.
21. The agent according to any one of the preceding embodiments, comprising human framework sequences, a proline residue at position 46 and the following complementarity determining regions (CDRs):
    a) a CDR-H1 comprising SEQ ID NO: 8;
    b) a CDR-H2 comprising SEQ ID NO: 9;
    c) a CDR-H3 comprising SEQ ID NO: 10;
    d) a CDR-L1 comprising SEQ ID NO: 5;
    e) a CDR-L2 comprising SEQ ID NO: 6; and
    f) a CDR-L3 comprising SEQ ID NO: 7.
22. The agent according to any one of the preceding embodiments in at least partially purified form.
23. The agent according to any one of the preceding embodiments in essentially isolated form.
24. The agent according to any one of the preceding embodiments, which is conjugated or fused to a second agent.
25. The agent according to embodiment 24, wherein the second agent is selected from a protracting group such as PEG, a cytotoxic agent, a detectable marker, a targeting agent.
26. The agent according to any one of the preceding embodiments for use as a pharmaceutical.
27. The agent according to any one of the preceding embodiments for use as a pharmaceutical in the treatment of malignant neoplasms, viral infections, an inflammatory disorder, and an autoimmune disease.
28. The agent according to any one of the preceding embodiments for use as a pharmaceutical for neutralising or reducing the inhibitory activity of a CD94/NKG2A receptor expressed on the surface of a cell in a human patient.
29. The agent according to any one of the preceding embodiments for use as a pharmaceutical for potentiating the cell-killing activity of a CD94/NKG2A expression cell in a human patient.
30. The agent according to any one of the preceding embodiments for use as a pharmaceutical in inducing killing of a Cw3 expressing target cell in a human patient.
31. A composition comprising an agent according to any one of the preceding embodiments together with a pharmaceutically acceptable carrier, diluent or vehicle.
32. A nucleic acid fragment encoding the agent according to any one of embodiments 9 and 10 insofar as these depend from embodiment 9.
33. The nucleic acid fragment according to embodiment 32, which is selected from a DNA and an RNA fragment.
34. A vector comprising the nucleic acid fragment according to embodiment 32 or 33.
35. The vector according to embodiment 34 which is selected from a cloning vector and an expression vector.
36. A transformed host cell which comprises the nucleic acid fragment according to embodiment 32 or 33, or the vector according to embodiment 34 or 35.
37. The transformed cell according to embodiment 36, which comprises
    (a) one nucleic acid fragment according to embodiment 32 or 33, which includes coding regions for both a heavy and a light chain amino acid sequence, said coding regions being under the control of the same or different regulatory genetic elements, or
    (b) two separate nucleic acid fragments according to embodiment 32 or 33, of which one encodes a light chain amino acid sequence and the other encodes a heavy chain amino acid sequence.
38. The transformed host cell according to embodiment 36 or 37, which expresses the nucleic acid fragment(s) according to embodiment 32 or 33.
39. A method for producing the transformed cell according to any one of embodiments 36-38, the method comprising transfecting or transducing a host cell with a vector according to embodiment 34 or 35, which encodes a heavy and light chain amino acid sequence, or with two different vectors according to embodiment 34 or 35 where one encodes a heavy chain amino acid sequence and the other encodes a light chain amino acid sequence.
40. A method for producing the agent according to embodiment 9 and 10-23 insofar as these depend from embodiment 9, comprising culturing the transformed host cell according to any one of the embodiments 36-38 under conditions which facilitate expression of the nucleic acid fragment of embodiment 32 or 33 and optionally recovering the expression product thus produced.
41. A method for treatment or amelioration of a malignant neoplasm, a viral infection, an inflammatory disorder, and an autoimmune disorder in a human patient in need thereof. comprising administering an effective amount of an agent according to any one of embodiments 1-25 or a composition according to embodiment 31 to said human patient.
42. The method according to embodiment 41, wherein said malignant neoplasm is selected from the group consisting of squamous cell carcinoma, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, Burketts lymphoma, multiple myeloma, acute or chronic myelogenous leukemias, promyelocytic leukemia, fibrosarcoma, rhabdomyoscarcoma; melanoma, seminoma, teratocarcinoma, neuroblastoma, glioma, astrocytoma, neuroblastoma, glioma, schwannomas, fibrosarcoma, rhabdomyoscaroma, osteosarcoma, melanoma, xeroderma pigmentosum. keratoacanthoma, seminoma, thyroid follicular cancer, teratocarcinoma, other carcinoma of the bladder, breast, colon, kidney, liver, lung, ovary, prostate, pancreas, stomach, cervix, thyroid or skin, other hematopoietic tumors of lymphoid lineage, other hematopoietic tumors of myeloid lineage, other tumors of mesenchymal origin, other tumors of the central or peripheral nervous system, or other tumors of mesenchymal origin.

43. The method according to embodiment 42, wherein the malignant neoplasm is selected from multiple myeloma, Non-Hodgkins lymphoma and an acute myelogenous lymphoma.
44. The method according to embodiment 41, wherein said autoimmune disorder is selected from the group consisting of hemolytic anemia, pernicious anemia, polyarteritis nodosa, systemic lupus erythematosus, Wegener's granulomatosis, autoimmune hepatitis, Behcet's disease, Crohn's disease, primary bilary cirrhosis, scleroderma, ulcerative colitis, Sjogren's syndrome, Type 1 diabetes mellitus, uveitis, Graves' disease, Alzheimer's disease, thyroiditis, myocarditis, rheumatic fever, scleroderma, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, Bullous pemphigoid, Hashimoto's thyroiditis, psoriasis, and vitiligo.
45. The method according to embodiment 41, wherein said inflammatory disorder is selected from the group consisting of adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, selerochoroiditis, scrotitis, sinusitis, spondylitis, steatitis, stomatitis, synovitis, syringitis, tendonitis, tonsillitis, urethritis, and vaginitis.
46. The method according to embodiment 41, wherein said viral infection is selected from the group consisting of hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2).
47. An isolated human or humanized antibody that
    (a) binds to an extra-cellular portion of human CD94/NKG2A receptor expressed on the surface of a CD94/NKG2A-expressing lymphocyte;
    (b) reduces the inhibitory activity of the human CD94/NKG2A receptor; and
    (c) does not compete with HLA-E in binding the human CD94/NKG2A receptor and/or can bind the CD94/NKG2A receptor simultaneously with HLA-E and/or does not prevent the binding of HLA-E to the CD94/NKG2A receptor.
48. The antibody of embodiment 47, which is an anti-NKG2 antibody that binds to CD94/NKG2A with a KD at least a 100-fold lower than to CD94/NKG2C.
49. The human or humanized antibody of any of embodiments 47-48, which competes with Z199 antibody in binding to human CD94/NKG2A.
50. The human or humanized antibody of any of embodiments 47-49, which binds to the same epitope on CD94/NKG2A as Z199 antibody.
51. The human or humanized antibody of any of embodiments 47-50, which binds to a segment in the NKG2A sequence (SEQ ID NO:11) comprising, in alternative embodiments
    (a) P94-N107 and/or M189-E197;
    (b) P94 to N107; or
    (c) M189 to E197.
52. The humanized antibody of any of embodiments 47-51, which is humanized Z199 antibody.
53. The humanized antibody of any of embodiment 52, comprising amino acid residues Y31, L49, and P94 of the Z199 VL domain (SEQ ID NO:2), and amino acid residues Y57, Y102, and P103 of the Z199 VL domain (SEQ ID NO:4).
54. The humanized antibody of any of embodiments 52-53, comprising at least one back-mutation in the variable-heavy (VH) or variable light (VL) domain.
55. The humanized antibody of any of embodiments 52-54, comprising amino acid residue P45 of the Z199 VL domain.
56. The humanized antibody of any of embodiments 52-55, comprising amino acid residues 24-33, 49-55, and 88-96 of the Z199 VL domain, and amino acid residues 31-35, 50-60, 62, 64, 66, and 99-108 of the Z199 VH domain.
57. The humanized antibody of any of embodiments 52-56, comprising an inserted amino acid in CDR_L1.
58. The humanized antibody of embodiment 57, wherein the inserted amino acid is a serine (S) inserted between residues 30 and 31 of the Z199 VL domain.
59. The humanized antibody of any of embodiments 52-58, comprising one or more of amino acid residues Q1, W46, V57, and S69 of the Z199 VL domain and/or one or more of amino acid residues A49, T78, and T97 of the Z199 VH domain.
60. An isolated antibody binding human CD94/NKG2A receptor and comprising
    (a) a CDR-L1 comprising SEQ ID NO:5;
    (b) a CDR-L2 comprising SEQ ID NO:6;
    (c) a CDR-L3 comprising SEQ ID NO:7.
    (d) a CDR-H1 comprising SEQ ID NO:8;
    (e) a CDR-H2 comprising SEQ ID NO:9;
    (f) a CDR-H3 comprising SEQ ID NO:10;
    (g) human scaffold sequences; and
    (h) a proline (P) residue at Kabat position 46.
61. The antibody of any of embodiments 47-60, comprising an IgG4 constant region, optionally comprising an S241P mutation.
62. The antibody of any of embodiments 47-60, which is an antigen-binding antibody fragment.
63. The antibody of any of embodiments 47-60, which is conjugated or fused to a second agent.
64. The antibody of embodiment 63, wherein the second agent is selected from a protracting group such as PEG, a cytotoxic agent, a detectable marker, and a targeting agent.
65. The antibody of any of embodiments 47-64, or an antigen-binding fragment thereof, for use as a pharmaceutical.
66. The antibody of any of embodiments 47-64 for use in treating a malignant neoplasm, a viral infection, an inflammatory disorder, and/or an autoimmune disease.
67. The antibody of any of embodiments 47-64 for use in reducing the inhibitory activity of a CD94/NKG2A receptor expressed on the surface of a cell in a human patient.
68. The antibody of any of embodiments 47-64 for use in potentiating the cell-killing activity of a CD94/NKG2A expression cell in a human patient.
69. The antibody of any of embodiments 47-64 for use in inducing killing of a HLA-E expressing target cell in a human patient.
70. A composition comprising the antibody of any of embodiments 47-64 and a pharmaceutically acceptable carrier, diluent or vehicle.
71. A nucleic acid fragment encoding the antibody of any of embodiments 47-64.
72. The nucleic acid fragment of embodiment 70, which is a DNA or RNA fragment.
73. A vector comprising the nucleic acid fragment of embodiment 71 or 72.
74. The vector of embodiment 73 which is a cloning vector or an expression vector.

75. A transformed host cell comprising the nucleic acid fragment of embodiments 71 or 72, or the vector of embodiments 73 or 74.
76. The transformed cell of embodiment 75, comprising
    (a) a nucleic acid fragment according to embodiment 71 or 72, which includes coding regions for both a heavy and a light chain amino acid sequence, said coding regions being under the control of the same or different regulatory genetic elements, or
    (b) two separate nucleic acid fragments according to embodiment 71 or 72, of which one encodes a light chain amino acid sequence and the other encodes a heavy chain amino acid sequence.
77. The transformed host cell of embodiment 75 or 76, which expresses the nucleic acid fragment(s).
78. A method for producing the transformed cell of any of embodiments 76 and 77, the method comprising transfecting or transducing a host cell with the vector of embodiment 73 or 74, which encodes a heavy and light chain amino acid sequence, or with two different vectors according to embodiment 73 or 74 where one encodes a heavy chain amino acid sequence and the other encodes a light chain amino acid sequence.
79. A method for producing the antibody of any of embodiments 47-64, comprising culturing the transformed host cell of any of embodiments 75-77 under conditions which facilitate expression of the nucleic acid fragment(s) and optionally recovering the antibody produced.
80. A method for treatment or amelioration of a malignant neoplasm, a viral infection, an inflammatory disorder, and an autoimmune disorder in a human patient in need thereof, comprising administering an effective amount of the antibody of any of embodiments 47-64 or a composition according to embodiment 70 to said human patient.
81. The method according to embodiment 80, wherein said malignant neoplasm is selected from the group consisting of squamous cell carcinoma, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, Burketts lymphoma, multiple myeloma, acute or chronic myelogenous leukemias, promyelocytic leukemia, fibrosarcoma, rhabdomyoscarcoma; melanoma, seminoma, teratocarcinoma, neuroblastoma, glioma, astrocytoma, neuroblastoma, glioma, schwannomas, fibrosarcoma, rhabdomyoscaroma, osteosarcoma, melanoma, xeroderma pigmentosum, keratoacanthoma, seminoma, thyroid follicular cancer, teratocarcinoma, other carcinoma of the bladder, breast, colon, kidney, liver, lung, ovary, prostate, pancreas, stomach, cervix, thyroid or skin, other hematopoietic tumors of lymphoid lineage, other hematopoietic tumors of myeloid lineage, other tumors of mesenchymal origin, other tumors of the central or peripheral nervous system, or other tumors of mesenchymal origin.
82. The method according to embodiment 81, wherein the malignant neoplasm is selected from multiple myeloma, Non-Hodgkins lymphoma and a acute myelogenous lymphoma.
83. The method according to embodiment 80, wherein said autoimmune disorder is selected from the group consisting of hemolytic anemia, pernicious anemia, polyarteritis nodosa, systemic lupus erythematosus, Wegener's granulomatosis, autoimmune hepatitis, Behcet's disease, Crohn's disease, primary bilary cirrhosis, scleroderma, ulcerative colitis, Sjogren's syndrome, Type 1 diabetes mellitus, uveitis, Graves' disease, Alzheimer's disease, thyroiditis, myocarditis, rheumatic fever, scleroderma, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, Bullous pemphigoid, Hashimoto's thyroiditis, psoriasis, and vitiligo.
84. The method according to embodiment 80, wherein said inflammatory disorder is selected from the group consisting of adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myosititis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, selerochoroiditis, scrotitis, sinusitis, spondylitis, steatitis, stomatitis, synovitis, syringitis, tendonitis, tonsillitis, urethritis, and vaginitis.
85. The method according to embodiment 80, wherein said viral infection is selected from the group consisting of hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2).

All references, including publications, patent applications and patents, cited herein are hereby incorporated by reference to the same extent as if each reference was individually and specifically indicated to be incorporated by reference and was set forth in its entirety herein. The citation and incorporation of patent documents herein is done for convenience only and does not reflect any view of their validity, patentability and/or enforceability.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A method of treating a malignant neoplasm comprising administering to a subject having a malignant neoplasm expressing human leukocytic antigen-E (HLA-E) an effective amount of an antibody binding human CD94/NKG2A receptor, said antibody comprising:
    (a) a CDR-L1 comprising SEQ ID NO:5;
    (b) a CDR-L2 comprising SEQ ID NO:6;
    (c) a CDR-L3 comprising SEQ ID NO:7;
    (d) a CDR-H1 comprising SEQ ID NO:8;
    (e) a CDR-H2 comprising SEQ ID NO:9;
    (f) a CDR-H3 comprising SEQ ID NO:10;
    (g) human VL and VH framework regions; and
    (h) a proline (P) residue at Kabat position 46 in the VL domain.

* * * * *

SEQUENCE LISTING

<160> NUMBER OF SEQ ID NOS: 16

<210> SEQ ID NO 1
<211> LENGTH: 321
<212> TYPE: DNA
<213> ORGANISM: Mus musculus

<400> SEQUENCE: 1

```
caaattgttc tcacccagtc tccagcactc atgtctgcgt ctccagggga gaaggtcacc      60
atgacctgca gtgccagctc aagtgtaagt tacatttact ggtaccagca gaagccaaga     120
tcctccccca aaccctggat ttatctcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtgg agtggtaacc cgtacacgtt cggaggggg      300 accaagctgg aaataaaacg g                                                321
```

<210> SEQ ID NO 2
<211> LENGTH: 107
<212> TYPE: PRT
<213> ORGANISM: Mus musculus

<400> SEQUENCE: 2

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys Arg
            100                 105
```

<210> SEQ ID NO 3
<211> LENGTH: 357
<212> TYPE: DNA
<213> ORGANISM: Mus musculus

<400> SEQUENCE: 3

```
gaagttcaac tggtggagtc tgggggaggc ttagtgaagc ctggagggtc cctgaaactc      60
tcttgtgcag cctctggatt cactttcagt agctatgcca tgtcttgggt tcgccagtct     120
ccagagaaga ggctggagtg ggtcgcagaa attagtagtg gtggtagtta cacctactat     180
ccagacactg tgaccggccg attcaccatc tccagagaca atgccaagaa cacccttgtac    240
```

```
ctggaaatca gcagtctgag gtctgaggac acggccatgt attactgtac aaggcatggt      300
gactacccta ggttcttcga tgtctggggc gcaggacca cggtcaccgt ctcctca          357
```

<210> SEQ ID NO 4
<211> LENGTH: 119
<212> TYPE: PRT
<213> ORGANISM: Mus musculus

<400> SEQUENCE: 4

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser
        115
```

<210> SEQ ID NO 5
<211> LENGTH: 11
<212> TYPE: PRT
<213> ORGANISM: Artificial
<220> FEATURE:
<223> OTHER INFORMATION: Humanized sequence

<400> SEQUENCE: 5

```
Ser Ala Ser Ser Ser Val Ser Ser Tyr Ile Tyr
1               5                   10
```

<210> SEQ ID NO 6
<211> LENGTH: 7
<212> TYPE: PRT
<213> ORGANISM: Artificial
<220> FEATURE:
<223> OTHER INFORMATION: Humanized sequence

<400> SEQUENCE: 6

```
Leu Thr Ser Asn Leu Ala Ser
1               5
```

<210> SEQ ID NO 7
<211> LENGTH: 9
<212> TYPE: PRT
<213> ORGANISM: Artificial
<220> FEATURE:
<223> OTHER INFORMATION: Humanized sequence

<400> SEQUENCE: 7

```
Gln Gln Trp Ser Gly Asn Pro Tyr Thr
1               5
```

<210> SEQ ID NO 8
<211> LENGTH: 5

```
<212> TYPE: PRT
<213> ORGANISM: Artificial
<220> FEATURE:
<223> OTHER INFORMATION: Humanized sequence

<400> SEQUENCE: 8

Ser Tyr Ala Met Ser
1               5

<210> SEQ ID NO 9
<211> LENGTH: 17
<212> TYPE: PRT
<213> ORGANISM: Artificial
<220> FEATURE:
<223> OTHER INFORMATION: Humanized sequence

<400> SEQUENCE: 9

Glu Ile Ser Ser Gly Gly Ser Tyr Thr Tyr Tyr Ala Asp Ser Val Lys
1               5                   10                  15

Gly

<210> SEQ ID NO 10
<211> LENGTH: 10
<212> TYPE: PRT
<213> ORGANISM: Artificial
<220> FEATURE:
<223> OTHER INFORMATION: Humanized sequence

<400> SEQUENCE: 10

His Gly Asp Tyr Pro Arg Phe Phe Asp Val
1               5                   10

<210> SEQ ID NO 11
<211> LENGTH: 233
<212> TYPE: PRT
<213> ORGANISM: Homo sapiens

<400> SEQUENCE: 11

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
                20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
        50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ser Pro Ser Ser Trp Ile Gly
                165                 170                 175
```

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
        210                 215                 220

Ile Ile Tyr His Cys Lys His Lys Leu
225                 230

<210> SEQ ID NO 12
<211> LENGTH: 107
<212> TYPE: PRT
<213> ORGANISM: Artificial
<220> FEATURE:
<223> OTHER INFORMATION: Germline construct

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Gln Gly Thr Lys Leu Glu Ile Lys
            100                 105

<210> SEQ ID NO 13
<211> LENGTH: 107
<212> TYPE: PRT
<213> ORGANISM: Artificial
<220> FEATURE:
<223> OTHER INFORMATION: Humanized sequence

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Gly Asn Pro Tyr
                85                  90                  95

Thr Phe Gly Gln Gly Thr Lys Leu Glu Ile Lys
            100                 105

<210> SEQ ID NO 14
<211> LENGTH: 117
<212> TYPE: PRT
<213> ORGANISM: Artificial

<220> FEATURE:
<223> OTHER INFORMATION: Germline construct

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Tyr Gly Met Asp Val Trp Gly Gln Gly Thr Thr
            100                 105                 110

Val Thr Val Ser Ser
        115

<210> SEQ ID NO 15
<211> LENGTH: 119
<212> TYPE: PRT
<213> ORGANISM: Artificial
<220> FEATURE:
<223> OTHER INFORMATION: Humanized sequence

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Pro Arg Phe Phe Asp Val Trp Gly Gln Gly
            100                 105                 110

Thr Thr Val Thr Val Ser Ser
        115

<210> SEQ ID NO 16
<211> LENGTH: 138
<212> TYPE: PRT
<213> ORGANISM: Homo sapiens

<400> SEQUENCE: 16

Ile Pro Phe Leu Glu Gln Asn Asn Ser Ser Pro Asn Thr Arg Thr Gln
1               5                   10                  15

Lys Ala Arg His Cys Gly His Cys Pro Glu Glu Trp Ile Thr Tyr Ser
            20                  25                  30

Asn Ser Cys Tyr Tyr Ile Gly Lys Glu Arg Arg Thr Trp Glu Glu Ser
        35                  40                  45

-continued

```
Leu Leu Ala Cys Thr Ser Lys Asn Ser Ser Leu Leu Ser Ile Asp Asn
    50                  55                  60

Glu Glu Glu Met Lys Phe Leu Ala Ser Ile Leu Pro Ser Ser Trp Ile
65                  70                  75                  80

Gly Val Phe Arg Asn Ser Ser His His Pro Trp Val Thr Ile Asn Gly
                85                  90                  95

Leu Ala Phe Lys His Lys Ile Lys Asp Ser Asp Asn Ala Glu Leu Asn
                100                 105                 110

Cys Ala Val Leu Gln Val Asn Arg Leu Lys Ser Ala Gln Cys Gly Ser
        115                 120                 125

Ser Met Ile Tyr His Cys Lys His Lys Leu
130                 135
```